US007605301B2

(12) United States Patent
Yao et al.

(10) Patent No.: US 7,605,301 B2
(45) Date of Patent: Oct. 20, 2009

(54) PLANT FAD2 CODING SEQUENCE BALANCING FOR FATTY ACID PROFILING IN EDIBLE OILS

(75) Inventors: Kening Yao, Saskatoon (CA); Derek A. Potts, Saskatoon (CA); Katherine M. Lockhart, Saskatoon (CA); Daryl R. Males, Saskatoon (CA)

(73) Assignee: Viterra, Inc., Regina, Saskatchewan (CA)

(*) Notice: Subject to any disclaimer, the term of this patent is extended or adjusted under 35 U.S.C. 154(b) by 385 days.

(21) Appl. No.: 10/330,775

(22) Filed: Dec. 26, 2002

(65) Prior Publication Data

US 2003/0221217 A1 Nov. 27, 2003

(51) Int. Cl.
*A01H 1/00* (2006.01)
*A01H 5/00* (2006.01)
*C12N 15/82* (2006.01)

(52) U.S. Cl. ........................ 800/281; 800/285; 800/278

(58) Field of Classification Search ....................... None
See application file for complete search history.

(56) References Cited

U.S. PATENT DOCUMENTS

| | | | | |
|---|---|---|---|---|
| 4,554,101 A | 11/1985 | Hopp | ...................... | 260/112.5 |
| 5,625,130 A | 4/1997 | Grant et al. | ................. | 800/200 |
| 5,668,299 A | 9/1997 | DeBonte et al. | ............. | 800/230 |
| 5,840,946 A | 11/1998 | Wong et al. | ................. | 554/224 |
| 5,850,026 A | 12/1998 | DeBonte et al. | ............. | 800/281 |
| 5,861,187 A | 1/1999 | DeBonte et al. | ............. | 426/601 |
| 6,084,157 A | 7/2000 | DeBonte et al. | ............. | 800/306 |
| 6,303,849 B1 * | 10/2001 | Potts et al. | .................. | 800/306 |
| 6,787,686 B2 * | 9/2004 | Potts et al. | .................. | 800/306 |

FOREIGN PATENT DOCUMENTS

WO WO 96/27285 9/1996

OTHER PUBLICATIONS

Potts et al. 1999, The proceedings of 10th International Rapeseed Congress in Sep. 26-29, Canberra, Australia.*

Kim et al. 1994, Plant Molecular Biology 24: 105-117.*

Agnihotri, A., Kaushik, N., Singh, N. K., Raney, J. P. and Downey, R. K. 1995. Selection for better agronomical and nutritional characteristics in Indian rapeseed-mustard. Proc. 9.sup. th Int. Rapeseed Cong., Cambridge, U.K. vol. 2:425-427.

Altschul et al., 1990, J. Mol. Biol. 215:403-10.

Ames, B. N. 1983. Dietary carcinogens and anticarcinogens. Science 221:1256-1264.

Ausubel, et al. (eds), 1989, Current Protocols in Molecular Biology, vol. 1, Green Publishing Associates, Inc., and John Wiley & Sons, Inc., New York, at p. 2.10.3.

Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.

Downey, R. K. and Rakow, G. F. W. 1987. Rapeseed and mustard. In: Principles of cultivar development. W. R. Fehr, ed. Macmillian, N.Y. pp. 437-486.

Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081-1084.

Food Chemicals Codex. 1996. 4.sup. th Edition. Committee on Food Chemicals Codex, Food and Nutrition Board, Institute of Medicine, National Academy of Sciences. National Academy Press, Washington. pp. 77-79.

Griffiths et al., Biochem. J. 252: 641-647, 1988.

Henikoff and Henikoff, 1992, Proc. Natl. Acad. Sci. USA 89: 10915-10919.

Jeong et al., Proceedings of the 3rd National Plant Lipid Cooperative Meeting, 1999, South Lake Tahole, California.

Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.

Love, H. K., Rakow, G., Raney, J. P. and Downey, R. K. 1990. Development of low glucosinolate mustard. Can. J. Plant Sci. 70:419-424.

Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. vol. 1:164-169.

Marillia and Taylor, Plant Physiol. 120: 339, 1999.

McDonald, B. E. 1995. Oil properties of importance in human nutrition. In: *Brassica* Oilseeds: Production and Utilization. D. S. Kimber and D. I. McGregor, eds., CAB International, Oxon, U.K., pp. 291-299.

Miquel and Browse, J. Bio. Chem. 267: 1502-1509, 1992.

Napoli et al., 1990 Plant Cell 2: 279-289.

Needleman and Wunsch, 1970, J. Mol. Biol. 48:443.

Okuley et al., Plant Cell 6: 147-158,1994.

(Continued)

*Primary Examiner*—Elizabeth F McElwain
*Assistant Examiner*—Li Zheng
(74) *Attorney, Agent, or Firm*—Jondle & Associates, P.C.

(57) ABSTRACT

In one aspect, the invention provides novel tetraploid *Brassica* plants having no more than two expressible FAD2 coding sequences, capable of producing canola quality oils. Other aspects of the invention provide new variants of the FAD2 enzyme, comprising BjFAD2-b and BjFAD2-a, as well as nucleic acid sequences encoding such peptides. Other aspects of the invention include nucleic acid sequences upstream from the BjFAD2-b or BjFAD2-a ORFs. Other aspects of the invention include transgenic plants and plant pads. Vectors capable of transforming plant cells are provided, comprising the nucleic acids of the invention, including FAD2 coding sequences. Corresponding methods are provided for obtaining the transgenic plants of the invention. Methods are provided for using the plants of the invention, including selected plants and transgenic plants, to obtain plant products. Amplification primers for identifying the FAD2 coding sequences of the invention are provided, together with methods of obtaining plants using the FAD2 coding sequences of the invention as markers.

2 Claims, 13 Drawing Sheets

OTHER PUBLICATIONS

Pearson and Lipman, 1988, Proc. Natl. Acad. Sci. USA 85: 2444.
Potts and Males. 1999. Inheritance of fatty acid composition in *Brassica juncea*. The proceedings of 10th International Rapeseed Congress in Sep. 26-29, 1999; Canberra, Australia; CD-ROM.
Potts et al., 1999. Canola-quality *Brassica juncea*, a new oilseed crop for the Canadian prairies, The proceedings of 10th International Rapeseed Congress in Sep. 26-29, 1999; Canberra, Australia; CD-ROM.
Rakow, G. 1991. Canola quality mustard. Proc. Special Cropportunities I: A conference organized by the Crop Development Centre and the Extension Division, University of Saskatchewan, Saskatoon, Canada pp. 55-59.
Rakow, G., Raney, J. P. and Males, D. 1995. Field performance of canola quality *Brassica juncea* Proc. 9.sup.th Int. Rapeseed Congress, Cambridge, U.K. vol. 2:428-430.
Raney, P., Rakow, G. and Olson, T. 1995. Development of zero erucic, low linolenic *Brassica juncea* utilizing interspecific crossing. Proc. 9.sup.th Int. Rapeseed Congress, Cambridge, U.K. vol. 2:413-415.
Shanklin and Somerville, Proc. Natl. Acad. Sci. USA 88: 2510-2514, 1991.
Shanklin et al., Biochemistry 33: 12787-12794, 1994.
Singh et al., 1995. Plant Physiol. 109: 1498.
Stotjesdijk et al., 1999. Genetic manipulation for altered oil quality in *Brassica*. The proceedings of 10th International Rapeseed Congress in Sep. 26-29, 1999; Canberra, Australia; CD-ROM.
Swanson, E. B., Coumans, M. P., Brown, G. L., Patel, J. D. and Beversdorf, W. D. 1988. The characterization of herbicide tolerant plants in *Brassica napus* L. after in vitro selection of miscrospores and protoplasts. Plant Cell Rep. 7:83-87.
Swanson, E. B., Herrgesell, M. J., Arnoldo, M., Sippell, D. W. and Wong, R. S. C. 1989. Microspore mutagenesis and selection: canola plants with field tolerance to the imidazolinones. Theor. Appl. Genet. 78:525-530.
Tanhuanpää et al., Mol. Breed. 4: 543-550, 1998.
Thiagarajah, M. R. and Stringham, G. R. 1993. A comparison of genetic segregation in traditional and microspore-derived populations of *Brassica juncea* L. Czern and Coss. Plant Breeding 111:330-334.
Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.
Zhu et al., 1999. Proc. Natl. Acad. Sci. 96: 8768-8773.
Zhu et al., 2000. Nature Biotechnology 18: 555-558.
Smith, Temple. F., et al., "Comparison of Biosequences", *Advances in Applied Mathematics* 2: 482-489 (1981).
Tijssen, "Overview of principles of hybridization and the strategy of nucleic acid probe assays", *Laboratory Techniques in Biochemistry and Molecular Biology—Hybridization with Nucleic Acid Probes*, pp. 19-78 (1993).
Dellaporta, Stephen, L. et al., "A Plant DNA Minipreparation: Version II", *Plant Molecular Biology Reporter* 1: 19-21 (1983).

* cited by examiner

FIGURE 1A

```
ATGGGTGCAG GTGGAAGAAT GCAAGTGTCT CCTCCCTCGA AGAAGTCTGA   50
AACCGACACC ATCAAGCGCG TACCCTGCGA GACACCGCCC TTCACTGTCG  100
GAGAACTCAA GAAAGCAATC CCACCGCACT GTTTCAAACG CTCGATCCCT  150
CGCTCTTTCT CCTACCTCAT CTGGGACATC ATCATAGCCT CCTGCTTCTA  200
CTACGTCGCC ACCACTTACT TCCCTCTCCT CCCTCACCCT CTCTCCTACT  250
TCGCCTGGCC TCTCTACTGG GCCTGCCAGG GCTGCGTCCT AACCGGCGTC  300
TGGGTCATAG CCCACGAGTG CGGCCACCAC GCCTTCAGCG ACTACCAGTG  350
GCTTGACGAC ACCGTCGGTC TCATCTTCCA CTCCTTCCTC CTCGTCCCTT  400
ACTTCTCCTG GAAGTACAGT CATCGACGCC ACCATTCCAA CACTGGCTCC  450
CTCGAGAGAG ACGAAGTGTT TGTCCCCAAG AAGAAGTCAG ACATCAAGTG  500
GTACGGCAAG TACCTCAACA ACCCTTTGGG ACGCACCGTG ATGTTAACGG  550
TTCAGTTCAC TCTCGGCTGG CCTTTGTACT TAGCCTTCAA CGTCTCGGGA  600
AGACCTTACG ACGGCGGCTT CGCTTGCCAT TTCCACCCTA ACGCTCCCAT  650
CTACAACGAC CGCGAGCGTC TCCAGATATA CATCTCCGAC GCTGGCATCC  700
TCGCCGTCTG CTACGGTCTC TACCGCTACG CTGCTGTCCA AGGAGTTGCC  750
TCGATGGTCT GCTTCTACGG AGTCCCGCTT CTGATAGTCA ACGGGTTCTT  800
AGTTTTGATC ACTTACTTGC AGCACACGCA TCCTTCCCTG CCTCACTACG  850
ATTCGTCTGA GTGGGATTGG TTGAGGGGAG CGTTGGCTAC CGTTGACAGA  900
GACTACGGGA TCTTGAACAA GGTCTTCCAC AATATCACGG ACACGCACGT  950
GGCGCATCAC CTGTTCTCGA CCATGCCGCA TTATCACGCG ATGGAAGCTA 1000
CCAAGGCGAT AAAGCCGATA CTGGGAGAGT ATTATCAGTT CGATGGGACG 1050
CCGGTGGTTA AGGCGATGTG GAGGGAGGCG AAGGAGTGTA TCTATGTGGA 1100
ACCGGACAGG CAAGGTGAGA AGAAAGGTGT GTTCTGGTAC AACAATAAGT 1150
TATGA                                                  1155
```

FIGURE 1B

| | | | | | |
|---|---|---|---|---|---|
| MGAGGRMQVS | PPSKKSETDT | IKRVPCETPP | FTVGELKKAI | PPHCFKRSIP | 50 |
| RSFSYLIWDI | IIASCFYYVA | TTYFPLLPHP | LSYFAWPLYW | ACQGCVLTGV | 100 |
| WVIAHECGHH | AFSDYQWLDD | TVGLIFHSFL | LVPYFSWKYS | HRRHHSNTGS | 150 |
| LERDEVFVPK | KKSDIKWYGK | YLNNPLGRTV | MLTVQFTLGW | PLYLAFNVSG | 200 |
| RPYDGGFACH | FHPNAPIYND | RERLQIYISD | AGILAVCYGL | YRYAAVQGVA | 250 |
| SMVCFYGVPL | LIVNGFLVLI | TYLQHTHPSL | PHYDSSEWDW | LRGALATVDR | 300 |
| DYGILNKVFH | NITDTHVAHH | LFSTMPHYHA | MEATKAIKPI | LGEYYQFDGT | 350 |
| PVVKAMWREA | KECIYVEPDR | QGEKKGVFWY | NNKL | | 384 |

FIGURE 1C

```
ATGGGTGCAG GTGGAAGAAT GCAGGTTTCT CCTTCTCCCA AGAAGTCCGA   50
AACCGATACC CTCAAGCGTG TTCCCTGCGA GACGCCTCCC TTCACAGTAG  100
GAGAGCTCAA GAAAGCCATC CCACCGCACT GTTTCAAACG CTCCATCCCT  150
CGCTCCTTCT CCTACCTCAT CTGGGACATC ATCGTAGCCT CCTGCTTCTA  200
CTACGTCGCC ACCACCTACT TTCCCCTCCT CCCTCACCCT CTCTCTTACA  250
TTGCTTGGCC TCTCTACTGG GCCTGCCAAG GCTGCGTCCT AACCGGCGTC  300
TGGGTCATAG CCCACGAATG CGGCCACCAC GCTTTCAGCG ACTACCAGTG  350
GCTAGACGAC ACCGTCGGTC TCATCTTCCA TTCCTTCCTC CTCGTCCCTT  400
ACTTCTCCTG GAAGTACAGT CACCGCCGTC ACCATTCCAA CACCGGCTCG  450
CTCGAGAGAG ACGAGGTGTT TGTCCCCAAG AAAAAATCAG ACATCAAGTG  500
GTACGGCAAG TACCTCAACA ACCCTCTCGG ACGCACCGTG ATGCTAACCG  550
TCCAGTTCAC TCTCGGCTGG CCCTTGTACT TGGCCTTCAA CGTCTCGGGC  600
AGACCTTACC CCGAGGGGTT CGCCTGCCAT TTCCACCCGA ACGCTCCCAT  650
CTACAACGAC CGCGAACGCC TCCAGATATA CGTCTCCGAC GCTGGTATCC  700
TCGCCGTCTG TTACGGTCTC TACCGTTACG CGGCCGCGCA GGGAGTGGCC  750
TCGATGGTCT GCCTCTACGG AGTTCCGCTT CTGATAGTCA ACGCGTTCCT  800
CGTCTTGATC ACTTACTTGC AGCACACTCA TCCTTCGTTG CCTCACTACG  850
ACTCCTCTGA GTGGGATTGG TTGAGGGGAG CTTTGGCTAC CGTTGACAGA  900
GACTACGGAA TCTTGAACAA GGTCTTCCAC AACATCACGG ACACGCACGT  950
GGCGCATCAT CTGTTCTCCA CGATGCCGCA TTATCACGCG ATGGAGGCCA 1000
CGAAGGCCAT AAAGCCGATA CTGGGAGACT ATTACCAGTT CGATGGGACA 1050
CCATGGGTTA AGGCGATGTG GAGGGAGGCG AAGGAGTGTA TCTATGTTGA 1100
ACCGGACAGG CAAGGTGAGA AGAAAGGTGT GTTCTGGTAC AACAATAAGT 1150
TATGA                                                  1155
```

FIGURE 1D

| | | | | | |
|---|---|---|---|---|---|
| MGAGGRMQVS | PSPKKSETDT | LKRVPCETPP | FTVGELKKAI | PPHCFKRSIP | 50 |
| RSFSYLIWDI | IVASCFYYVA | TTYFPLLPHP | LSYIAWPLYW | ACQGCVLTGV | 100 |
| WVIAHECGHH | AFSDYQWLDD | TVGLIFHSFL | LVPYFSWKYS | HRRHHSNTGS | 150 |
| LERDEVFVPK | KKSDIKWYGK | YLNNPLGRTV | MLTVQFTLGW | PLYLAFNVSG | 200 |
| RPYPEGFACH | FHPNAPIYND | RERLQIYVSD | AGILAVCYGL | YRYAAAQGVA | 250 |
| SMVCLYGVPL | LIVNAFLVLI | TYLQHTHPSL | PHYDSSEWDW | LRGALATVDR | 300 |
| DYGILNKVFH | NITDTHVAHH | LFSTMPHYHA | MEATKAIKPI | LGDYYQFDGT | 350 |
| PWVKAMWREA | KECIYVEPDR | QGEKKGVFWY | NNKL | | 384 |

```
gaagccaagc acgatcctcc attctcaact ttatagcatt tttttctttt   50
ctttccggct accactaact tctacagttc tacttgtgag tcggcaagga  100
cgtttcctca tattaaagta aagacatcaa ataccataat cttaatgcta  150
attaacgtaa cggatgagtt ctataacaca acccaaacta gtctttgtga  200
acattaggat tgggtaaacc aatatttaca ttttaaaaac aaaatacaaa  250
aagaaacgtg ataaacttta taaaagcaat tatatgatca cggcatcttt  300
ttcacttttc cgtaaatata tataagtggt gtaaatatca gatatttgga  350
gtagaaaaaa aaaaaaaaaa aaaagaaata tgaagagagg aaataatgga  400
ggggcccact agtaaaaaag aaagaaaaga gatgtcactc aatcgtctca  450
cacgggcccc cgtcaattta aacggcctgc cttctgccca atcgcatctt  500
accagaacca gagagattca ttaccaaaga gatagagaga gaaagagagg  550
agacagagag agtttgagga ggtgcttctt cgtagggttc atcgttatta  600
acgttaaatc ttcatccccc tacgtcaacc agctcaaggt ccctttcttc  650
ttccatttcc tctcattttt acgttgtttt caatcttggt ctgttctttt  700
cttatcgctt ttctattcta tctatcattt ttgcttttca gtcgatttaa  750
ttctagacct gttaatattt attgcattaa actatagatc tgttcttgat  800
tctctgtttt cttgtgtgaa atcttgatgc tgtctttacc attaatctga  850
ttatattgtc tataccttgg agaatatgaa atgttgcatt ttcatttgtc  900
cgaatacaaa ctgtttgact ttcaatcttt tttaatgatt tattttgatg  950
ggttggtgga gttgaaaaat caccatagca gtctcacgtc ctggtcttag 1000
aaatatcctt cctattcaaa gttatatata tttgtttact tgtcttagat 1050
ctggacctga gacatgtaag tacctatttg ttgaatcttt gggtaaaaaa 1100
cttatgtctc tgggtaaaat ttgcttggag atttgaccga ttcctattgg 1150
ctcttgattc tgtaattacg taatacatga aaaatgtttc atttggccta 1200
tgctcacttc atgcttataa actttttctt gcaaattaat tggattagat 1250
gctccttcat agattcagat gcaatagatt tgcatgaaga aaataataga 1300
attcatgata gtaaaaagat tgtatttttg tttgtttgtt tatgtttaaa 1350
agtctatatg ttgacaatag agttgctatc aactgtttca tttagtttat 1400
gtttttgtca agttgcttat tctaagagac attgtgatta tgacttgtct 1450
tctctaacgt agtttagtaa taaaagacga aagaaattga tatccacaag 1500
```

(FIGURE 6A continued)

```
aaagagatgt aagctgtaac gtatcaaatc tcattaataa ctagtagtat 1550
tctcaacgct atcgtttatt tctttctttg gtttgccact atatgccgct 1600
tctctcctct tttgtcccac gtactatcca ttttttgaa actttaataa 1650
cgtaacactg aatattaatt tgttggttta attaactttg agtttgtttt 1700
tggtttatgc agaaacATGG GTGCAGGTGG AAGAATGCAA GTGTCTCCTC 1750
CCTCGAAGAA GTCTGAAACC GACACCATCA AGCGCGTACC CTGCGAGACA 1800
CCGCCCTTCA CTGTCGGAGA ACTCAAGAAA GCAATCCCAC CGCACTGTTT 1850
CAAACGCTCG ATCCCTCGCT CTTTCTCCTA CCTCATCTGG GACATCATCA 1900
TAGCCTCCTG CTTCTACTAC GTCGCCACCA CTTACTTCCC TCTCCTCCCT 1950
CACCCTCTCT CCTACTTCGC CTGGCCTCTC TACTGGGCCT GCCAGGGCTG 2000
CGTCCTAACC GGCGTCTGGG TCATAGCCCA CGAGTGCGGC CACCACGCCT 2150
TCAGCGACTA CCAGTGGCTT GACGACACCG TCGGTCTCAT CTTCCACTCC 2220
TTCCTCCTCG TCCCTTACTT CTCCTGGAAG TACAGTCATC GACGCCACCA 2250
TTCCAACACT GGCTCC                                     2166
```

FIGURE 6B

```
gaagccaagc acgatcctcc attctcccac ttttagcatt tctttttttt   50
ttttctttct ttccggctac cacttacttg tacttgtaag tcgagtcggt  100
aagaacgttt cctcatatta aactaaagac atcatatatc gtcgccttga  150
tgctaattaa cgtaaccgat gaaaactgta acagaatcca aaccaatctc  200
tctggatatt tggattacca gtgggtcaac caatatttac tttttttcag  250
aacgaaacac aaaaggaaac ttgataaact ttataaaagt aaacataaat  300
atattcagta ttcactgcct ctttttctgc ttttccgtaa atacataagt  350
gccgtaaata tcagatattt ggaatagaaa agtaataaag gaaaaaaata  400
tgaggagagg aaaaaaagag gggcccagtt gtaaaaaaaa gagagatgtc  450
cactcaatcc tcttctctct cattctttta cccacgggcc gtcaatttaa  500
acggcctagc ttctgcccca tttgcttctg accagaaacc acagagagag  550
agagagtttc attaccaaag agagagagat aggagagaga agatagagag  600
agtctgcgga ggagcttctt cgtagggttc atcgttatta acgttaaatc  650
tctatccccc tacgtcagcc agctcaaggt cccctcttc ttcttcttct  700
tccatttctt ctcattttac gtttttttatc ttcttcaatc ttttgaacct  750
tttctggtct gtggtaatct tattccctct tatcattttg cgcttcaatc  800
gatttcatta tagatctgac aatattgatt gcattcaact atagatctgg  850
tagcgattct ctgtttccat gttaaaatct gttgctgtct tttactattg  900
ttatggttat tgtctatatc gtcgagtata tgaaatgttg cattttcatt  950
ttgttcaaat acgtaagtgt ttgactatct aatttcgatc gttattttta 1000
attatatata ttattgatcg gttggtagag ttgaaaaaaa ttcaccagaa 1050
atattatgcg tagcagcctc accgtcctgg ttataaaatc atcccatctg 1100
tttattcaaa agttatatac tactatttgt ttagatctgg acctgagtat 1150
atgtaaagct gtattatctt tgttaaattt gctcctattt gttgaatctt 1200
tggcagattt gaccgattcc tattcgcttc ttggtactgt aattacatag 1250
taaatggaaa aattttcatt ggctgcgtgt aaaaaaaaaa aaagaagttc 1300
cattgactta tgctagaact caaactcttg ctcataaacc ttttgtagta 1350
caaattaatt gaatatgggg taggtaaact caggaatctt tcatagattc 1400
agatgcaaat agagctgcat gtagaaaata ataggattca tgacagtaaa 1450
aagaagattg gtactatgtt ttgtttgttt ctgtttaaaa gtctatatga 1500
```

(In the line beginning at position 1001, "tatatata" following "at" is printed bold and underlined.)

(FIGURE 6B continued)

```
ttgacaataa tatttgttgc tctcaaattc tctctactgt ttcatttagc 1550
tttttttttt ttggccaagt tgatatccaa gaggaatagt gattatggct 1600
gctatcttaa aaaaatcgat atccgcaaga aagagatgtg agctgtagcg 1650
tatcaaatct tattcattta ctagtcgtat tctcaacgct atcgtttatt 1700
tctttttctt tcttcggttt gccactaaaa gccgcttccc tgctctttgt 1750
tacacttagt atccattttt gtggtagtcc atttttgaa acgtaacatt 1800
gaatgttttg tctgaaaaaa aaaatttgat ggtttaataa attcttattc 1850
tcgcatagac atttgtcagt taagattaat aagtctttag ctttggacat 1900
tgagtttcag ctcctgattg aagtctttgc ttttgttttt ttttccttgc 1950
agaaaacaAT GGGTGCAGGT GGAAGAATGC AGGTTTCTCC TTCTCCCAAG 2000
AAGTCCGAAA CCGATACCCT CAAGCGTGTT CCCTGCGAGA CGCCTCCCTT 2050
CACAGTAGGA GAGCTCAAGA AAGCCATCCC ACCGCACTGT TTCAAACGCT 2100
CCATCCCTCG CTCCTTCTCC TACCTCATCT GGGACATCAT CGTAGCCTCC 2150
TGCTTCTACT ACGTCGCCAC CACCTACTTT CCCCTCCTCC CTCACCCTCT 2200
CTCTTACATT GCTTGGCCTC TCTACTGGGC CTGCCAAGGC TGCGTCCTAA 2250
CCGGCGTCTG GGTCATAGCC CACGAATGCG GCCACCACGC TTTCAGCGAC 2300
TACCAGTGGC TAGACGACAC CGTCGGTCTC ATCTTCCATT CCTTCCTCCT 2350
CGTCCCTTAC TTCTCCTGGA AGTACAGTCA CCGCCGTCAC CATTCCAACA 2400
CCGGCTCG                                              2408
```

PLANT FAD2 CODING SEQUENCE BALANCING FOR FATTY ACID PROFILING IN EDIBLE OILS

CROSS REFERENCE TO RELATED APPLICATION

Right of priority is hereby claimed to Canada Patent Application No. 2,382,767, filed May 15, 2002.

FIELD OF THE INVENTION

The invention is in the field of plant biology, involving compositions and methods related to fatty acid metabolism in plants. Aspects of the invention include genes and enzymes involved in fatty acid metabolism in plants, as well as plants and plant parts having the genes and expressing the enzymes, and methods for making the plants and plant parts using the genes (including recombinant genetic engineering methods and classical plant breeding methods using markers of the invention).

BACKGROUND OF THE INVENTION

Fatty acids are acyl lipids that are found in a variety of plant tissues, including the triacylglycerols in oil bodies of seeds and fruits, as well as the glycolipids and phospholipids in leaves, roots or shoots. Fatty acids include saturated and unsaturated monocarboxylic acids with unbranched even-numbered carbon chains, such as the unsaturated fatty acids: oleic (18:1, et al. a C18 chain with a double bond), linoleic (18:2) and linolenic (18:3) acid.

Plants may synthesize fatty acids in plastids using acetyl-CoA and malonyl-CoA as substrates. At least 30 enzymatic reactions may be involved in multiple cycles of condensation, reduction of the 3-keto group, dehydration and reduction of the double bond, leading to synthesis of palmitoyl-ACP (16:0-ACP) and stearoyl-ACP (18:0-ACP). A soluble enzyme, stearoyl-ACP Δ9 desaturase may introduce a first double bond in the conversion of the fatty acid stearoyl-ACP to oleoyl-ACP (18:1-ACP) (Shanklin and Somerville, Proc. Natl. Acad. Sci. USA 88: 2510-2514, 1991). Acyl-ACPs may be used for plastid lipid synthesis through transfer of free fatty acids from ACP to glycerol-3-phosphate or monoacylglycerol-3-phosphate. Alternatively, free fatty acids may be released from ACP by acyl-ACP thioesterases. These free fatty acids may be used to form acyl-CoAs and for the synthesis of other plant lipids including storage lipids in seeds. Further desaturation of fatty acids may be carried out by membrane bound desaturases of a chloroplast and endoplasmic reticulum.

In Arabidopsis, two loci, FAD2 and FAD3, have been shown to affect the desaturation of extraplastid lipids, which may lead to the synthesis of polyunsaturated fatty acids (Miquel and Browse, J. Bio. Chem. 267: 1502-1509, 1992.). Specifically, synthesis of the polyunsaturated fatty acids linoleic acid (Δ9,12-18:2) and α-linolenic acid (Δ9,12,15-18:3) may begin with the conversion of oleic acid (Δ9-18:1) to linoleic acid, the enzymatic step may be catalyzed by microsomal ω-6 oleic acid desaturase (FAD2). The linoleic acid may then be converted to α-linolenic acid through further desaturation by ω-3 linoleic acid desaturase (FAD3). Coding sequences of FAD2 genes have been reported in several *Brassica* species (Tanhuanpää et al., Mol. Breed. 4: 543-550, 1998; Singh et al., Plant Physiol. 109: 1498, 1995; Marillia and Taylor, Plant Physiol. 120: 339, 1999).

Mutational inactivation of a FAD2 gene has been reported in some species. For example, in cultured peanut, a mutation in the PFAD2-A gene coding sequences results in a non-functional protein (Jeong et al., Proceedings of the 3rd National Plant Lipid Cooperative Meeting, 1999. South Lake Tahole, Calif.). The *Arabidopsis* FAD2 mutant line FAD2-5, caused by T-DNA insertion into the FAD2 gene, shows increased oleic acid content (Okuley et al., Plant Cell 6: 147-158,1994).

Significant efforts have been made to manipulate the fatty acid profile of plants, particularly oil-seed varieties such as *Brassica* spp. that are used for the large-scale production of commercial fats and oils (see for example U.S. Pat. No. 5,625,130 issued to Grant et al. 29 Apr. 1997; U.S. Pat. No. 5,668,299 issued to DeBonte et al. 16 Sep. 1997; U.S. Pat. No. 5,840,946 issued to Wong et al. 24 Nov. 1998; U.S. Pat. No. 5,850,026 issued to DeBonte et al. 15 Dec. 1998; U.S. Pat. No. 5,861,187 issued to DeBonte et al. 19Jan. 1999; and U.S. Pat. No. 6,084,157 issued to DeBonte et al. 4 Jul. 2000).

An increase in the oleic acid content of plant oils may be desirable for some applications. For human consumption, vegetable oils rich in oleic acid may be considered superior products compared to oils rich in polyunsaturated fatty acids. The term "canola" has been used to describe varieties of *Brassica* spp. containing low erucic acid ($\Delta^{13}$-22:1) and low glucosinolates. For example, in the U.S., under 21 CFR 184.1555, low erucic acid rapeseed oil derived from *Brassica napus* or *Brassica campestris* is recognized as canola oil where it has an erucic acid content of no more than 2% of the component fatty acids (Table I sets out the Food Chemicals Codex (1996) specifications for canola oil). Plant breeders have also selected canola varieties that are low in glucosinolates, such as 3-butenyl, 4-pentenyl, 2-hydroxy-3-butenyl or 2-hydroxy-4-pentenyl glucosinolate. Canola quality meal may for example be defined as having a glucosinolate content of less than 30 micromoles of aliphatic glucosinolates per gram of oil-free meal. Currently, the principle commercial canola crops comprise *B. napus* and *B. rapa* (*campestris*) varieties.

TABLE I

Food Chemicals Codex (1996) Specifications for Canola Oil

| Property | Canola Oil |
|---|---|
| Fatty Acids, % by weight | |
| <14 | <0.1 |
| 14:0 myristic | <0.2 |
| 16:0 palmitic | <6.0 |
| 16:1 | <1.0 |
| 18:0 | <2.5 |
| 18:1 oleic | >50.0 |
| 18:2 linoleic | <40.0 |
| 18:3 linolenic | <14.0 |
| 20:0 | <1.0 |
| 20:1 | <2.0 |
| 22:0 | <0.5 |
| 22:1 erucic | <2.0 |
| 24:0 | <0.2 |
| 24:1 | <0.2 |
| Acid value | <6 |
| Cold Test | Passes test |
| Colour (AOCS-Wesson) | <1.5R/15Y |
| Free fatty acids (as oleic) | <0.05% |
| Heavy metals (as Pb) | ≦5 mg/kg |
| Iodine value | 110-126 |
| Lead | <0.1 mg/kg |
| Peroxide value | ≦10 meq/kg |
| Refractive index | 1.465-1.467 |
| Saponifiable value | 178-193 |

TABLE I-continued

| Food Chemicals Codex (1996) Specifications for Canola Oil | |
|---|---|
| Property | Canola Oil |
| Stability | ≧7 h |
| Sulfur | ≦10 mg/kg |
| Unsaponifiable matter | ≦1.5% |
| Water | ≦0.1% |

*B. juncea* is an amphidiploid plant of the *Brassica* genera that is generally thought to have resulted from the hybridization of *B. rapa* and *B. nigra*. Under some growing conditions, *B. juncea* may have certain superior traits to *B. napus* and *B. rapa*. These superior traits may include higher yield, better drought and heat tolerance and better disease resistance. However, as a source of oils for human consumption, *B. juncea* is generally thought to have a less desirable fatty acid profile compared to the current canola crops. For example, the original wild type *B. juncea* varieties may contain low oleic acid (~20%) and high erucic acid in the seed oil.

In the early 1980's, a low erucic acid *B. juncea* was reported (Kirk and Oram, J. Aust. Inst. Agric. Sci. 47: 51-52, 1981). However, this low erucic acid *B. juncea* also reportedly contains low oleic acid and high linoleic acid. Continued breeding efforts have focused on lowering the linoleic acid content and increasing the oleic acid content of *B. juncea* seed oil. Cosuppression strategies targeting FAD2 have for example recently been used to produce genetically modified *B. napus* and *B. juncea* varieties having elevated oleic acid content (Stotjesdijk et al., 1999). The relative unpredictability of cosuppression and antisense approaches may, however, detract from the usefulness of this approach in efficiently generating new varieties.

U.S. Pat. No. 6,303,849 issued to Potts et al. on 16 Oct. 2001 (incorporated herein by reference) discloses *B. juncea* lines having an edible oil that has properties similar to canola. The *B. juncea* lines disclosed therein have a lineage that includes *B. juncea* lines J90-3450 and J90-4316, deposited as ATCC Accession Nos 203389 and 203390 respectively (both of which were deposited by Agriculture and Agri-Food Canada under the terms of the Budapest Treaty on 23 Oct. 1998 at the American Type Culture Collection, 10801 University Blvd., Manassas, Va. USA 20110-2209). There remains a need for novel varieties of *B. juncea* having favourable fatty acid profiles.

SUMMARY OF THE INVENTION

In one aspect of the invention, it has unexpectedly been discovered that the fatty acid profile of edible oils derived from oil seeds may be altered by balancing the activity of FAD2 enzymes, so that in a tetraploid plant or an amphidiploid plant no more than two FAD2 coding sequences are expressible. In one aspect, the invention accordingly provides for the deletion or silencing of selected FAD2 coding sequences in a tetraploid plant, such as in lines of *B. juncea*. For example, in some embodiments the FAD2 gene from only one of the two FAD2 loci in the amphidiploid *B. juncea* genome is transcribed. In some embodiments, amphidiploid plants having no more than two expressible FAD2 coding sequences may exhibit a high oleic acid content phenotype, so that an edible oil derived from the plant may be characterized by one or more of the following characteristics: an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated fatty acid content of less than 7.1% by weight. In some embodiments, the invention provides low erucic acid oil derived from tetraploid plants having no more than two expressible FAD2 coding sequences, such as novel *B. juncea* plants, that will meet one or more of the specifications for low erucic acid rapeseed oil in the Food Chemicals Codex, 4th edition (1996), as set out above.

Alternative aspects of the invention include plants and plant parts. As used herein, "plant parts" includes plant cells, seeds, pollen bearing the nucleic acids of the invention or expressing the FAD2 enzymes of the invention or having the FAD2 coding sequences of the invention or having sequences upstream of the FAD2 coding region (including the regulatory region). Methods are provided for using the plants of the invention, including progeny plants selected by markers of the invention, to obtain plant products. As used herein, "plant products" includes anything derived from a plant of the invention, including plant parts such as seeds, meals, fats or oils, including plant products having altered oleic acid concentrations. Methods are provided for modifying plants with two or more FAD2 coding sequences, comprising inactivating one or more of the FAD2 coding sequences so that the plant has no more than two expressible FAD2 coding sequences. For example, such methods may involve inactivating one or more of the FAD2 loci in a genome so that the plant has no more than two expressible FAD2 coding sequences.

Amplification primers for identifying portions of the FAD2 coding sequences of the invention are provided, which may be used for example to distinguish different alleles of a selected FAD2 locus. Methods are provided for obtaining plants using the FAD2 coding sequences of the invention, or regions upstream of the FAD2 coding sequences of the invention. For example, sequences of the invention may be used to guide or target site-specific mutations that may down-regulate expression of selected FAD2 coding sequences, such as by down-regulating the expression of a FAD2 gene from a selected FAD2 locus. Methods are provided for modifying plants with two or more FAD2 gene loci, comprising inactivating one or more of the FAD2 gene loci so that the plant has no more than two expressible FAD2 coding sequences. Amplification primers for identifying the FAD2 gene loci and different alleles of a selected FAD2 gene locus of the invention are provided, together with methods for obtaining plants using the FAD2 loci/alleles of the invention, or regions upstream of the FAD2 loci/alleles of the invention.

BRIEF DESCRIPTION OF THE DRAWINGS

FIG. 1A shows the nucleotide sequence of the open reading frame (ORF) of the BjFAD2-a gene (SEQ ID NO: 3).

FIG. 1B shows the amino acid sequence of the BjFAD2-a protein (SEQ ID NO: 4).

FIG. 1C shows the nucleotide sequence of the ORF of the BjFAD2-b gene (SEQ ID NO: 5).

FIG. 1D shows the amino acid sequence of the BjFAD2-b protein (SEQ ID NO: 6).

FIG. 6A shows the nucleotide sequence of the upstream non-coding region (lower case) plus 450 bp ORF (upper case) of the BjFAD2-a gene (SEQ ID NO: 13). The TATA box is shown in bold and underlined.

FIG. 6B shows the nucleotide sequence of the upstream non-coding region (lower case) plus 450 bp ORF (upper case) of the BjFAD2-b gene (SEQ ID NO: 14). The TATA box is shown in bold and underlined.

DETAILED DESCRIPTION OF THE INVENTION

Figure 2:
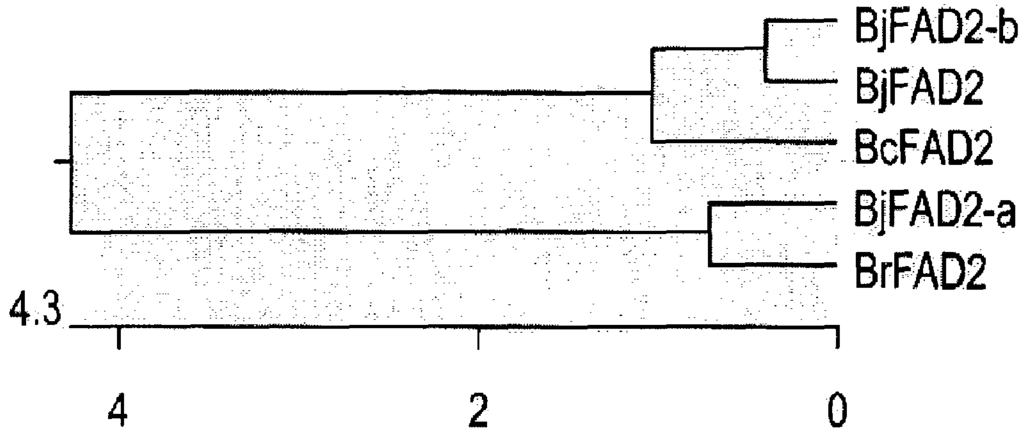
FIG. 2 shows a phylogenetic analysis of the relationships among *Brassica* FAD2 nucleotide sequences aligned by the CLUSTAL program. The analyzed sequences with accession numbers and species names are indicated: *B. rapa* sequence is designated BrFAD2 (AF042841); *B. carinata* sequence is designated BcFAD2 (AF124360); a previously isolated *B. juncea* sequence is designated BjFAD2 (X91139); two *B. juncea* sequences isolated in this invention are designated BjFAD2-a and BjFAD2-b, respectively. The scale beneath the tree measures the distance between sequences.

In one aspect, the invention comprises a tetraploid plant, such as an amphidiploid *Brassica juncea* plant, having no more than two expressible FAD2 coding sequences, et al. no expressible FAD2 coding sequence, one expressible FAD2 coding sequence or two expressible FAD2 coding sequences. Where there are two expressible FAD2 coding sequences, the coding sequences may be the same or may be different. In various aspects of the invention, the FAD2 coding sequence may be selected from the group consisting of open reading frames from *B. juncea* FAD2-b, *B. juncea* FAD2, *B. carinata* FAD2, *B. juncea* FAD2-a, *B. napus* FAD2, *B. oleracea* FAD2, *B. nigra* FAD2 and *B. rapa* FAD2.

In various aspects, the invention involves the modulation of the number of copies of an expressible coding sequence in a plant genome. By "expressible" it is meant that the primary structure, et al. sequence, of the coding sequence indicates that the sequence encodes an active protein. Expressible coding sequences may nevertheless not be expressed as an active protein in a particular cell. This 'gene silencing' may for example take place by various mechanisms of homologous transgene inactivation in vivo. Homologous transgene inactivation has been described in plants where a transgene has been inserted in the sense orientation, with the unexpected result that both the gene and the transgene were down-regulated (Napoli et al., 1990 Plant Cell 2: 279-289). The exact molecular basis for such cosuppression is unknown, although there are at least two putative mechanisms for inactivation of homologous genetic sequences. Transcriptional inactivation via methylation has been suggested as one mechanism, where duplicated DNA regions signal endogenous mechanisms for gene silencing. A post-transcriptional mechanism has also been suggested, where the combined levels of expression from both the gene and the transgene are thought to produce high levels of transcript which trigger threshold-induced degradation of both messages (van Bokland et al., 1994, Plant J. 6: 861-877). In the present invention, the expressible coding sequences in a genome may accordingly not all be expressed in a particular cell. For example, in some embodiments the FAD2 gene from only one of the two FAD2 loci in the amphidiploid *B. juncea* genome is expressible, and of the two expressible coding sequences at that locus only one may actually be expressed in a particular cell.

In alternative embodiments, the invention provides *Brassica juncea* plants wherein the activity of a fatty acid desaturase is altered or the oleic acid content is altered relative to WTBJ. By fatty acid desaturase, it is meant that a protein exhibits the activity of introducing a double bond in the biosynthesis of a fatty acid. For example, FAD2 enzymes may be characterized by the activity of introducing the second double bond in the biosynthesis of linoleic fatty acids (C18:2). Altered desaturase activity may include an increase, reduction or elimination of a desaturase activity compared to a reference plant, cell or sample.

In other aspects, reduction of desaturase activity may include the elimination of expression of a nucleic acid sequence that encodes a desaturase, such as a nucleic acid sequence of the invention. By elimination of expression, it is meant herein that a functional amino acid sequence encoded by the nucleic acid sequence is not produced at a detectable level. Reduction of desaturase activity may include the elimination of transcription of the a nucleic acid sequence that encodes a desaturase, such as a sequence of the invention encoding a FAD2 enzyme. By elimination of transcription it is meant herein that the mRNA sequence encoded by the nucleic acid sequence is not transcribed at detectable levels. Reduction of desaturase activity may also include the production of a truncated amino acid sequence from a nucleic acid sequence that encodes a desaturase. By production of a truncated amino acid sequence it is meant herein that the amino acid sequence encoded by the nucleic acid sequence is missing one or more amino acids of the functional amino acid sequence encoded by a wild type nucleic acid sequence. In addition, reduction of desaturase activity may include the production of a variant desaturase amino acid sequence. By production of a variant amino acid sequence it is meant herein that the amino acid sequence has one or more amino acids that are different from the amino acid sequence encoded by a wild type nucleic acid sequence. A variety of mutations may be introduced into a nucleic acid sequence for the purpose of reducing desaturase activity, such as frameshift mutations, substitutions and deletions. For example, mutations in coding sequences may be made so as to introduce substitutions within functional motifs in a desaturase, such as the motif comprising three-histidine amino residues at amino acids 105-110, 141-145, and 316-320 of FAD2.

In some embodiments, the invention provides new FAD2 polypeptide sequences, which may be modified in accordance with alternative embodiments of the invention. It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (et al., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, et al. differing by more than 2.0. For example, on this basis, the following amino acid substitutions for the wild type His (−0.5) at a position corresponding to amino acid 105 in BjFAD2-b would be non-conserved substitutions: Trp (−3.4), Arg (+3.0); Lys (+3.0); Asp (+3.0); Glu (+3.0).

In alternative embodiments, conserved amino acid substitutions may be made where an amino acid residue is substituted for another having a similar hydropathic index (et al., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, et al. differing by more than 2.0. For example, on this basis, the following amino acid substitutions for the wild type His (−3.2) at a position corresponding to amino acid 105 in BjFAD2-b would be non-conserved substitutions: Ile (+4.5); Val (+4.2); Leu (+3.8); Phe (+2.8); Cys (+2.5); Met (+1.9); Ala (+1.8); Gly (−0.4); Thr (−0.7); Ser (−0.8); and Trp (−0.9).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

Various aspects of the present invention encompass nucleic acid or amino acid sequences that are homologous to other sequences. As the term is used herein, an amino acid or nucleic acid sequence is "homologous" to another sequence if the two sequences are substantially identical and the functional activity of the sequences is conserved (for example, both sequences function as or encode a selected enzyme or promoter function; as used herein, the term 'homologous' does not infer evolutionary relatedness). Nucleic acid sequences may also be homologous if they encode substantially identical amino acid sequences, even if the nucleic acid sequences are not themselves substantially identical, a circumstance that may for example arise as a result of the degeneracy of the genetic code.

Two nucleic acid or protein sequences are considered substantially identical if, when optimally aligned, they share at least about 25% sequence identity in protein domains essential for conserved function. In alternative embodiments, sequence identity may for example be at least 50%, 70%, 75%, 90%, 95% or 99%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci.* USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, *J. Mol. Biol.* 215:403-10 (using the published default settings). Software for performing BLAST analysis may be available through the National Center for Biotechnology Information (through the Internet at .ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992, *Proc. Natl. Acad. Sci.* USA 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs). The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9,1,0.87); PAM70 (10,1,0.87) BLOSUM80 (10,1,0.87); BLOSUM62 (11,1,0.82) and BLOSUM45 (14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, *Current Protocols in Molecular Biology*). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

In further aspects of the invention, methods of plant breeding are provided that comprise crossing parent tetraploid or amphidiploid strains to produce a hybrid tetraploid or amphidiploid progeny plant having no more than two expressible FAD2 coding sequences. In some embodiments, the parent strains may have 0, 1 or 2 expressible FAD2 coding sequences. By tetraploid, it is meant that a genome consists of four chromosome sets. By amphidiploid, it is meant that a genome consists of two diploid chromosome sets, providing four chromosome sets in total. Amphidiploid *Brassica* plants include *B. juncea, B. napus* and *B. carinata*. Other amphidiploid plants include Triticale. Amphidiploid plants may for example be resynthesized by crossing diploids and treating cells with colchicine.

Amphidiploids are a special subclass of allotetraploid plants. Allotetraploids have two sets of different genomes. If two plant species are crossed, they may have genomes that differ sufficiently so that the chromosomes from each genome will not pair with a homologue in the other genome during meiosis (chromosomes in such genomes may be said to be homeologous, that is they are similar but not close enough to pair). In such plants, unpaired chromosomes fail to undergo normal meiosis and the hybrid will, typically, be sterile. However, if the genome of the hybrid is doubled to produce an allotetraploids plant, the two sets chromosomes from each genome may pair with each other. Allotetraploids are generally fertile because they exhibit diploid like meiosis, in which case the allotetraploid plant may be referred to as amphidiploids. The homeologous genomes in an amphidiploid plant allow for fixed heterozygosity. Fixed heterozygosity occurs when a particular locus on the first genome is homozygous dominant, for example AA, but the same locus on the second genome is homozygous recessive, aa. Because no crossing over occurs between these two genomes, all the gametes produced will be genotype Aa and all the progenies produced from crossing genotype AAaa×AAaa will be AAaa. In the present invention, fixed heterozygosity may facilitate the stable inheritance of a selected ratio of expressed (or expressible) to non-expressed (or non-expressible) FAD2 coding sequences. For example, where a first parent amphidiploid strain and a second parent amphidiploid strain each have two expressed FAD2 coding sequences, or each have a single expressed FAD2 coding sequence, the progeny may stably inherit the parental ratio of expressed to non-expressed FAD2 coding sequences so that the progeny plant has no more than two expressed FAD2 coding sequences. Where there are two expressed FAD2 coding sequences, the FAD2 coding sequences may of course be the same or may be different.

In various aspects, the invention provides methods of modifying a *Brassica* plant, such as *Brassica juncea*, wherein the plant has more than two FAD2 coding sequences, for example in a tetraploid or amphidiploid genome, comprising inactivating one or more of the FAD2 coding sequences so that the plant has no more than two expressible FAD2 coding sequences. In alternative aspects, the invention provides a method of modifying a *Brassica* plant, wherein the plant has two FAD2 coding sequences, comprising inactivating one of the FAD2 coding sequences so that the plant has one expressed FAD2 coding sequences.

In one aspect, the invention provides a recombinant nucleic acid encoding a plant fatty acid desaturase, wherein the nucleic acid encodes a BjFAD2-b coding sequence (SEQ ID NO: 5). As used herein, the term "BjFAD2-b nucleic acid sequences", means the naturally occurring nucleic acid sequences, and portions thereof, encoding the *B. juncea* microsomal ω-6 oleic acid desaturase BjFAD2-b enzyme. BjFAD2-b (SEQ ID NO: 5) shares approximately 99.2% identity with the BjFAD sequence reported by Singh et al. (1995). In alternate aspects, the invention provides an isolated protein (SEQ ID NO: 6) encoded by the BjFAD2-b nucleic acid (SEQ ID NO: 5). In other aspects, the invention provides the nucleic acid sequence (SEQ ID NO: 16) upstream of the BjFAD2-b nucleic acid sequence (SEQ ID NO: 5). SEQ ID NO: 16 may include regulatory regions (including the TATA box) of the BjFAD2-b gene.

In alternate aspects, the invention provides a recombinant nucleic acid encoding a plant fatty acid desaturase, wherein the nucleic acid encodes an coding sequence of BjFAD2-a (SEQ ID NO: 3). As used herein, the term "BjFAD2-a nucleic acid sequences", means the naturally occurring nucleic acid sequences, and portions thereof, encoding the *B. juncea* microsomal ω-6 oleic acid desaturase BjFAD2-a. BjFAD2-a (SEQ ID NO: 3) shares approximately 90.6% identity with the BjFAD2 sequence reported by Singh et al. (1995). In alternate aspects, the invention provides an isolated protein (SEQ ID NO: 4) encoded by the BjFAD2-a nucleic acid (SEQ ID NO: 3). In other aspects, the invention provides the nucleic acid sequence (SEQ ID NO: 17) upstream of the BjFAD2-a nucleic acid sequence (SEQ ID NO: 3). SEQ ID NO: 17 may include regulatory regions (including the TATA box) of the BjFAD2-a gene.

In one aspect, the invention provides use of a nucleic acid sequence to guide site-specific mutation in a regulatory region of a FAD2 gene. For example, sequence from the upstream region of the FAD2-b gene may be used to guide site-specific mutations in the FAD2-b regulatory region such as the TATA box in order to down-regulate expression of the FAD2-b gene. Similarly, sequence from the upstream region of the FAD2-a gene could be used to guide site-specific mutations in the FAD2-a regulatory region to down-regulate expression of the FAD2-a gene. This may be done in vitro or in vivo.

In one aspect, the invention provides amplification primers or probes that may be used to identify FAD2 nucleic acid sequences of the invention, such as the BjFAD2-b or BjFAD2-a nucleic acid sequences (SEQ ID NOS: 5 and 3 respectively) or the region upstream from the BjFAD2-b or BjFAD2-a genes (SEQ ID NOS: 16 and 17 respectively), from other nucleic acid sequences. For example, primers or probes may be synthesised that are complementary to portions of the naturally occurring oleate desaturase BjFAD2-b or BjFAD2-a coding sequence. Selected primers may be capable of distinguishing plants having high oleic acid content from plants having low oleic acid content. Such primers or probes may comprise 5 or more contiguous residues complementary to BjFAD2-b or BjFAD2-a.

In another aspect of the invention, selective hybridisation and amplification, using FAD2 locus-specific probes and primer pairs of the invention, may be used to generate an amplification pattern that may contribute to a collection of DNA fingerprints to identify the FAD2 genotype of a germplasm. FAD2 probes may for example include primers or probes synthesised from complementary portions of the naturally occurring coding sequences of the oleate desaturase FAD2 genes and from complementary portions upstream of the FAD2 genes.

One aspect of the invention, comprises a method of selecting plants, such as *B. juncea* seedlings, having a high oleic acid content by utilizing PCR primers to selectively amplify a desired BjFAD2-b or BjFAD2-a gene. This method may be used, for example, to ensure that selected progeny carry a desired coding sequence conferring a high oleic acid oil phenotype. In accordance with an embodiment of the method, seedlings of a first segregating backcross population, may be subjected to PCR analysis to detect the mutant BjFAD2-b nucleic acid and the mutant FAD2-a nucleic acid, and the selected plants backcrossed again to a recurrent parental line. The backcrossing and PCR analysis of the first seedling population may, for example, proceed through at least two more cycles to create a third segregating backcross seedling population, which may be self-pollinated to create a third seedling population. The third seedling population may be subjected to PCR analysis for the mutant BjFAD2-b nucleic acid, and for the mutant FAD2-a nucleic acid, and homozygotes may be selected for further pedigree breeding, such as breeding of an elite, high oleic acid content strain.

In various embodiments, the invention comprises plants containing the coding sequences of the genes encoding the desaturases of the invention. In some embodiments, such plants will exhibit altered fatty acid content in one or more tissues.

EXAMPLES

The following examples are provided to illustrate alternative embodiments of the invention in detail, but do not limit the scope of the invention.

A low erucic acid *B. juncea* was used as starting material (WTBJ) in a plant breeding program which led to the development of various aspects of the present invention. A mutant line was selected whose fatty acid profile showed increased content of oleic acid and decreased contents of linoleic acid and linolenic acid. Since this fatty acid profile is similar to that of canola, et al. low linoleic acid (~20%) and high oleic acid (~60%), this line was named canola quality *B. juncea* (CQBJ) (Potts and Males, 1999).

A comparison of the FAD2 genes in WTBJ and CQBJ has disclosed the genetic background for elevated content of oleic acid in CQBJ. Two FAD2 loci, BjFAD2-a and BjFAD2-b, were isolated from WTBJ but BjFAD2-b was found to have been deleted from the CQBJ genome. Sequence analysis of ORFs indicates that BjFAD2-a and BjFAD2-b encode microsomal ω-6 fatty acid desaturases. Gene expression analysis suggests that BjFAD2-a and BjFAD2-b are co-expressed in WTBJ. In CQBJ, however, only BjFAD2-a may be expressed. The silence of BjFAD2-b expression in CQBJ may result in decrease in total microsomal ω-6 fatty acid desaturase activity in CQBJ. The resulting loss of expression of BjFAD2-b may cause the elevated accumulation of oleic acid in CQBJ.

In one aspect of the invention, the nucleotide sequences for ORFs of BjFAD2-a and BjFAD2-b may be used as a basis for engineering further modifications in the fatty acid profiles of CQBJ. For example, anti-sense cDNA specific for BjFAD2-a can be used to genetically engineer CQBJ in order to further increase the oleic acid content in *B. juncea*.

Upstream non-coding regions of BjFAD2-a and BjFAD2-b are also disclosed herein (including promoters having a "TATA" box and flanking sequence). The information from these nucleotide sequences may be used, for example, to design site-specific mutagenesis protocols that may result in modifications to the expression of FAD2 genes. Many techniques that can be used to generate site-specific mutations in plant genomes have been reported (see for example Zhu et al., 1999. Proc. Natl. Acad. Sci. 96: 8768-8773; Zhu et al., 2000. Nature Biotechnology 18: 555-558).

The high oleic acid trait associated with the deletion of the BjFAD2-b locus in the CQBJ lines may provide a valuable gene tag to mark the high oleic acid trait in *B. juncea* breeding programs. For example, when the CQBJ germplasm is crossed with *B. juncea* lines or varieties having low oleic acid content, a BjFAD2-b gene tag may be used for selection of the high oleic acid content trait in progeny plants. Primer pairs for BjFAD2-a and BjFAD2-b amplification are disclosed, and additional primer pairs may be designed with knowledge of the sequences disclosed in this invention.

Methods using site-specific mutagenesis to down-regulate FAD2 gene expression in selected coding sequences of *B. juncea* are disclosed in this invention. These methods, in addition to the use of BjFAD2-b sequences as gene tags for selecting for the trait of high oleic acid content, may be used in the search for such traits in other *B. juncea* populations (or in other *Brassica* species).

Example 1

Fatty Acid Profile Analysis of *B. juncea* Seeds

One perceived disadvantage of the low erucic acid *B. juncea* is that it contains only ~45% oleic acid in its seed oil compared to 60% oleic acid in canola oils. Using the low erucic acid *B. juncea* as starting material (WTBJ) a mutant line was selected that showed canola quality fatty acid profile (CQBJ). Crosses were made between the WTBJ and the CQBJ. F1-derived doubled haploid (DH) populations were produced. Fatty acid analysis of the self-pollinated seeds produced from the DH plants indicated that the modification of fatty acid profile is inherited as a single gene (Potts and Males, Proceedings of the 10$^{th}$ International Rapeseed Congress. 1999, Canberra, Australia, CD-ROM; U.S. Pat. No. 6,303,849).

For fatty acid analysis, 20 seeds from each self-pollinated DH line were homogenized in 2 ml of 0.5 N sodium methoxide in methanol and 1 ml of hexane that contained 500 ug of tripentadecanoin (TAG, G-15:0; Sigma). After adding 1 ml of water, the homogenate was centrifuged for 5 min at 3500 rpm using a bench top centrifuge (Baxter Canlab Megafuge 1.0, Heraeus Instruments). 200 ul of the top layer was transferred into an auto-sampler vial and 900 ul of hexane was added into each vial. 2 ul of this sample was injected into the gas-liquid chromatography (GLC; Hewlett Packard 5890), which was equipped with a DB-23 column (0.25 mm id×30 m; Hewlett Packard) and flame ionization detector. The GLC was operated with the injector and detector temperatures at 250° C. and 300° C., respectively. The column temperature was initially held at 160° C. for 0.5 min and gradually increase to 245° C. at the rate of 10° C./min, and then held at 245° C. for 4 min. Helium was used as a carrier gas with flow rate of 1 ml/min. The eluted fatty acid methyl esters were integrated. The identify of each peak was confirmed by comparison with the following authentic standards (Sigma): palmitic acid (16:0), palmitoleic acid (16:1), stearic acid (18:0), oleic acid (18:1, Δ9), cis-vaccenic acid (18:1, Δ11), linoleic acid (18:2), linolenic acid (18:3), eicosanoic acid (20:0), cis-11 eicosenoic acid (20:1), cis-11, 14 eicosadinoic acid (20:2), docosanoic acid (22:0), erucic acid (22:1), cis-13,16 docosadienoic acid (22:2), tetracosanoic acid (24:0) and cis-15 tetracosenoic acid (24:1).

Table 1A and 1B show the fatty acid profiles of mature seeds from representative DH lines of WTBJ and from representative DH lines of CQBJ, respectively. The fatty acid profiles are expressed as the percentage of each individual fatty acid in total fatty acids. The results clearly indicated that there is a dramatic difference in fatty acid profiles between WTBJ and CQBJ lines. Specifically, compared to the WTBJ lines, the linoleic acid was decreased from ~32% to ~20% with a concomitant increase in oleic acid from ~45% to ~60% in the CQBJ lines. This phenotype indicates that the mutation might occur in the FAD2 locus, the locus that controls the microsomal ω-6 oleic acid desaturase.

TABLE 1A

Fatty Acid Profiles of Mature Seeds from *Brassica juncea* lines with Low Oleic Acid.

| Lines | C16:0 | C16:1 | C18:0 | C18:1 | C18:2 | C18:3 | C20:0 | C20:1 | C20:2 | C22:0 | C22:1 | C22:2 | C24:0 | C24:1 |
|---|---|---|---|---|---|---|---|---|---|---|---|---|---|---|
| J92D-1356 | 3.89 | 0.20 | 2.05 | 44.50 | 33.18 | 12.98 | 0.59 | 1.42 | 0.15 | 0.32 | 0.04 | 0.00 | 0.24 | 0.40 |
| J96D-1112 | 3.84 | 0.17 | 2.17 | 45.54 | 32.43 | 12.77 | 0.59 | 1.40 | 0.15 | 0.29 | 0.03 | 0.00 | 0.23 | 0.36 |
| J96D-1241 | 3.84 | 0.20 | 1.82 | 45.39 | 32.37 | 13.23 | 0.57 | 1.43 | 0.15 | 0.31 | 0.04 | 0.00 | 0.22 | 0.38 |
| J96D-1323 | 3.83 | 0.19 | 1.74 | 44.51 | 33.26 | 13.48 | 0.53 | 1.33 | 0.15 | 0.28 | 0.03 | 0.00 | 0.22 | 0.40 |
| J96D-1336 | 3.85 | 0.17 | 2.11 | 44.97 | 32.63 | 13.14 | 0.58 | 1.43 | 0.14 | 0.29 | 0.04 | 0.00 | 0.22 | 0.37 |
| J96D-1348 | 3.79 | 0.20 | 1.79 | 44.61 | 32.88 | 13.66 | 0.55 | 1.38 | 0.15 | 0.30 | 0.03 | 0.00 | 0.21 | 0.39 |
| J96D-1523 | 3.82 | 0.19 | 2.01 | 46.83 | 31.48 | 12.49 | 0.59 | 1.44 | 0.14 | 0.30 | 0.03 | 0.00 | 0.24 | 0.38 |
| J96D-1582 | 3.88 | 0.19 | 1.78 | 46.70 | 31.75 | 12.63 | 0.55 | 1.35 | 0.14 | 0.11 | 0.29 | 0.04 | 0.20 | 0.36 |
| J96D-2525 | 3.99 | 0.19 | 1.91 | 46.25 | 31.20 | 13.05 | 0.60 | 1.44 | 0.13 | 0.32 | 0.04 | 0.00 | 0.30 | 0.40 |
| Average | 3.86 | 0.19 | 1.93 | 45.48 | 32.35 | 13.05 | 0.57 | 1.40 | 0.14 | 0.28 | 0.06 | 0.00 | 0.23 | 0.38 |

Note: The fatty acid profiles are expressed as percentage of each individual fatty acid in total fatty acids.
C16:0, palmitic acid;
C16:1, palmitoleic acid,
C18:0, stearic acid;
C18:1, sum of oleic acid (18:1, Δ9) and trace amount of cis-vaccenic acid (18:1, Δ11);
C18:2, linoleic acid;
C18:3, linolenic acid;
C20:0, eicosanoic acid;
C20:1, cis-11 eicosenoic acid; 20:2, cis-11, 14 eicosadinoic acid;
C22:0, docosanoic acid;
C22:1, erucic acid;
C22:2, cis-13, 16 docosadienoic acid;
C24:0, tetracosanoic acid; 24:1, cis-15 tetracosenoic acid.

TABLE 1B

Fatty Acid Profiles of Mature Seeds from *Brassica juncea* lines with High Oleic Acid.

| Lines | C16:0 | C16:1 | C18:0 | C18:1 | C18:2 | C18:3 | C20:0 | C20:1 | C20:2 | C22:0 | C22:1 | C22:2 | C24:0 | C24:1 |
|---|---|---|---|---|---|---|---|---|---|---|---|---|---|---|
| J96D-0899 | 3.88 | 0.24 | 1.96 | 61.73 | 18.05 | 10.92 | 0.61 | 1.52 | 0.10 | 0.34 | 0.00 | 0.00 | 0.24 | 0.38 |
| J96D-1537 | 3.91 | 0.24 | 2.32 | 59.18 | 20.40 | 10.36 | 0.73 | 1.54 | 0.09 | 0.39 | 0.03 | 0.00 | 0.32 | 0.45 |
| J96D-1540 | 3.81 | 0.22 | 2.37 | 60.83 | 18.39 | 11.01 | 0.67 | 1.59 | 0.10 | 0.34 | 0.00 | 0.00 | 0.25 | 0.38 |
| J96D-1542 | 3.83 | 0.21 | 2.05 | 60.66 | 19.98 | 9.96 | 0.62 | 1.52 | 0.08 | 0.33 | 0.03 | 0.00 | 0.27 | 0.40 |
| J96D-1562 | 3.84 | 0.20 | 2.18 | 59.01 | 20.94 | 10.37 | 0.66 | 1.53 | 0.10 | 0.35 | 0.04 | 0.00 | 0.30 | 0.43 |
| J96D-1612 | 3.84 | 0.18 | 2.13 | 59.56 | 19.67 | 11.21 | 0.64 | 1.48 | 0.09 | 0.08 | 0.34 | 0.04 | 0.31 | 0.38 |
| J96D-2449 | 3.79 | 0.20 | 2.28 | 61.12 | 18.60 | 10.62 | 0.69 | 1.45 | 0.07 | 0.00 | 0.37 | 0.04 | 0.29 | 0.44 |
| J96D-2455 | 3.83 | 0.23 | 2.46 | 61.09 | 18.97 | 9.86 | 0.73 | 1.52 | 0.08 | 0.00 | 0.38 | 0.04 | 0.33 | 0.42 |

TABLE 1B-continued

Fatty Acid Profiles of Mature Seeds from *Brassica juncea* lines with High Oleic Acid.

| Lines | C16:0 | C16:1 | C18:0 | C18:1 | C18:2 | C18:3 | C20:0 | C20:1 | C20:2 | C22:0 | C22:1 | C22:2 | C24:0 | C24:1 |
|---|---|---|---|---|---|---|---|---|---|---|---|---|---|---|
| J96D-2552 | 3.90 | 0.25 | 2.16 | 59.08 | 21.08 | 10.21 | 0.66 | 1.49 | 0.10 | 0.35 | 0.00 | 0.00 | 0.27 | 0.40 |
| Average | 3.85 | 0.22 | 2.21 | 60.25 | 19.56 | 10.50 | 0.67 | 1.52 | 0.09 | 0.24 | 0.13 | 0.01 | 0.29 | 0.41 |

Note: The fatty acid profiles are expressed as percentage of each individual fatty acid in total fatty acids.
C16:0, palmitic acid;
C16:1, palmitoleic acid,
C18:0, stearic acid;
C18:1, sum of oleic acid (18:1, A9) and trace amount of cis-vaccenic acid (18:1, Δ11);
C18:2, linoleic acid;
C18:3, linolenic acid;
C20:0, eicosanoic acid;
C20:1, cis-11 eicosenoic acid; 20:2, cis-11, 14 eicosadinoic acid;
C22:0, docosanoic acid;
C22:1, erucic acid;
C22:2, cis-13, 16 docosadienoic acid;
C24:0, tetracosanoic acid; 24:1, cis-15 tetracosenoic acid.

Example 2

Cloning and Sequence Analysis of the FAD2 Genes from *B. juncea*

To identify and characterize the allelic variations between WTBJ and CQBJ, two breeding lines were chosen for gene cloning and characterization. Line J92D-1356 was used as a WTBJ and line J96D-0899 was used as a CQBJ. Both lines were obtained through doubled haploid technique and are therefore homozygous in their genotype background. Self-pollinated seeds from each line were grown in a greenhouse under the conditions of 25° C. with light for 16 h and 20° C. without light for 8 hr. Young leaves were collected for DNA isolation and siliques at various developing stages were collected for isolation of total RNA. Developing siliques were collected 1, 2, 3 and 4 weeks after flowering and were designated stages I, II, III and IV, respectively.

The BjFAD2 genes were cloned by reverse transcriptase-polymerase chain reaction (RT-PCR). This would allow us to clone only the expressed members of the FAD2 gene family. A FAD2 gene sequence from *B. juncea* has been reported previously (Singh et al., 1995. Plant Physiol. 109: 1498; Accession No. X91139). Based on this published sequence we have designed forward primer FAD2up (SEQ ID NO: 1) and reverse primer FAD2low (SEQ ID NO: 2) in order to clone the open reading frame (ORF) of the FAD2 genes. For RNA isolation, 1 g of silique tissue from each stage was ground to fine powder in liquid nitrogen and the total RNA was extracted with TRIzol reagent (BRL) according to the manufacture's protocols. For RT reactions, 1 ug of total RNA was treated with amplification grade DNAase I (BRL) at room temperature for 15 min followed by heat inactivation at 65° C. for 10 min. Then the RT reactions were primed with primer FAD2low (SEQ ID NO: 2) using Superscript™ II reverse transcriptase (BRL) in a total volume of 20 ul. The reactions were incubated at 42° C. for 50 min followed by heat inactivation at 70° C. for 15 min. The PCRs were performed in a total volume of 50 μl containing the following: 2 μl of RT reaction, 200 μM each of dNTPs, 0.25 μM of primer FAD2up (SEQ ID NO: 1), 0.25 μM of primer FAD2low (SEQ ID NO: 2), 5 μl of 10×Pfu DNA polymerase buffer and 1 unit of Pfu DNA polymerase (BRL). Thirty cycles were performed for amplification using the cycling parameters of 40 s at 94° C., 40 s at 56° C., 2 min at 72° C. The PCR mixture was incubated at 94° C. for 5 min and 72° C. for 10 min before and after cycling, respectively. Fractionation of the PCR products on a 1% agarose gel indicated that a single DNA fragment was amplified. This DNA fragment was excised from the agarose gel and purified using a Geneclean II Kit (Bio101), which was then cloned into the SmaI site of pBluescript II KS (+) vector.

For sequence analysis of the RT-PCR products from WTBJ, a total of 11 clones from 3 separate experiments were randomly selected and the inserts were sequenced on both strands by a PRISM DyeDeoxy™ Terminator Cycle Sequencing Kit using a 377 DNA Sequencer. Sequence analysis was performed with the Lasergene DNA software (DNASTAR Inc.). Sequence alignment indicated that out of the 11 clones analyzed, 4 clones share an identical sequence, which is shown in FIG. 1A and designated BjFAD2-a (SEQ ID NO: 3). The other 7 clones share an identical sequence, which is shown in FIG. 1C and designated BjFAD2-b (SEQ ID NO: 4). The deduced amino acid sequences of the BjFAD2-a protein (SEQ ID NO: 5) and BjFAD2-b protein (SEQ ID NO: 6) are shown in FIG. 1B and FIG. 1D, respectively. Both sequences are 1155 bp in length and are homologous to other reported FAD2 sequences (Tanhuanpää et al., Mol. Breed. 4: 543-550, 1998; Singh et al., Plant Physiol. 109: 1498, 1995; Marillia and Taylor, Plant Physiol. 120: 339, 1999). The two sequences share 91.3% nucleotide sequence identity and 96.4% amino acid sequence identity with each other. In addition, both sequences displayed three histidine motifs at amino acid residues 105-110; 141-145; and 316-320, which are conserved in all oleate $\Delta^{12}$-desaturases and other membrane bound desaturases (Okuley et al., Plant Cell 6: 147-158, 1994; Shanklin et al., Biochemistry 33: 12787-12794, 1994; Singh et al., Plant Physiol. 109: 1498, 1995). These results confirmed that we have cloned two ORFs of the FAD2 gene from WTBJ. For sequence analysis of the RT-PCR products from CQBJ, we have analyzed 7 randomly selected clones from 2 separate RT-PCR experiments. Sequence analysis indicated that all 7 clones are identical to sequence of BjFAD2-a of the WTBJ (SEQ ID NO: 3).

Phylogenetic analysis with FAD2 gene sequences from other Brassica species indicated that the BjFAD2-a shares 98.6% nucleotide sequence identity with a FAD2 gene of *B. rapa* (A genome) (FIG. 2). The BjFAD2-b shares 98.4% nucleotide sequence identity with a FAD2 gene of *B. carinata* (BC genome). Since the nucleotide sequence identity between these two members is only at 91.3%, it is reasonable to predict that BjFAD2-a and BjFAD2-b belongs to genome A and genome B, respectively, of the *B. juncea* (AB genome). The previously isolated FAD2 gene from *B. juncea* shares nucleotide sequence identity of 90.6% and 99.2%, respectively, with the BjFAD2-a and BjFAD2-b (FIG. 2).

Example 3

Comparison of BjFAD2 Gene Expression Between WTBJ and CQBJ

Figure 3:
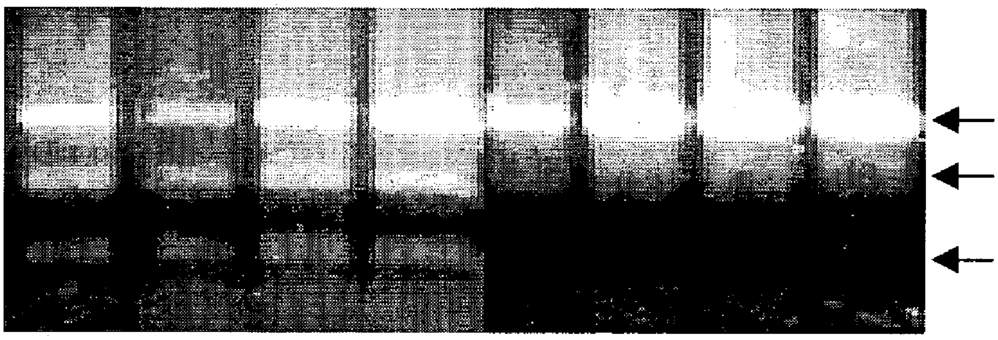
FIG. 3 shows electrophoretic analysis of BjFAD2 cDNAs after NotI restriction digestion. BjFAD2 cDNAs were synthesized by RT-PCR using RNAs isolated from WTBJ siliques at developing stages I ($W_1$), II ($W_2$) III ($W_3$) and IV ($W_4$) and from CQBJ siliques at developing stages I ($C_1$), II ($C_2$) III ($C_3$) and IV ($C_4$). The 1155 bp mark indicates the uncut cDNA of BjFAD2-a. The 730 bp and 425 bp marks indicate the cut fragments of BjFAD2-b.

Sequence analysis of the cloned RT-PCR products indicated that both BjFAD2-a and BjFAD2-b are expressed in WTBJ, whereas only the BjFAD2-a is expressed in CQBJ. To confirm that this result is not due to selection of colonies by chance, we performed restriction enzyme digestion of RT-PCR products. For this purpose, RT-PCR was performed using total RNA isolated from 4 stages of developing siliques of both WTBJ and CQBJ. Amplified cDNAs were then digested by NotI restriction enzyme and separated on 1% agarose gel by electrophoresis. Because BjFAD2-b cDNA contains a NotI site, it will be cut into two fragments of 730 bp and 425 bp. BjFAD2-a cDNA, however, does not contain a NotI site and therefore will not be cut by NotI restriction enzyme. The results are shown in FIG. 3. As we expected, the cDNAs from WTBJ generated 3 bands after NotI digestion, indicating the expression of both BjFAD2-a and BjFAD2-b in these developing siliques. However, a single top band was shown for the cDNAs from CQBJ after NotI digestion, confirming that indeed only the BjFAD2-a gene is expressed in CQBJ.

Northern Blot Analysis

Northern blot analysis was performed to evaluate the transcript levels of the FAD2 gene in CQBJ. Ten microgram of total RNAs isolated from developing siliques of both WTBJ and CQBJ were electrophoresed on 1% agarose-formaldehyde gels, blotted on nylon membrane and hybridized with the radiolabeled probe under the conditions of high stringency. A cDNA probe was prepared by labeling the gel purified BjFAD2-a fragment with [α-$^{32}$P]-dCTP using the RadPrime DNA Labeling System (BRL) according to the manufacture's protocols.

Figure 4:
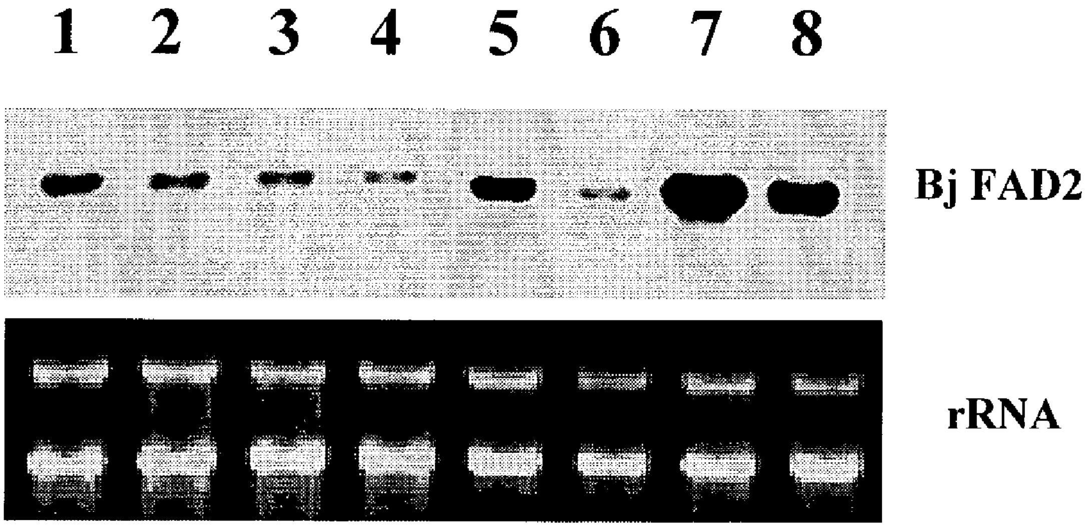
FIG. 4 shows results of BjFAD2 gene expression analysis. Total RNAs were isolated from siliques from WTBJ (lanes 1, 3, 5 and 7) and CQBJ (lanes 2, 4, 6 and 8), which were collected at developing stages I (lanes 1 and 2), II (lanes 3 and 4), III (lanes 5 and 6) and IV (lanes 7 and 8). Ten μg RNA was loaded on each lane and the membrane was hybridized with BjFAD2-a cDNA. Ribosomal RNA stained with ethidium bromide was shown to indicate equal amount of loading.

FIG. 4 shows the results of RNA gel blot analysis. The level of BjFAD2 gene expression for both WTBJ and CQBJ increases as siliques develop, with the highest expression level accruing at stage 4. However, the level of BjFAD2 expression in CQBJ was significantly lower than that in WTBJ at all stages. The results clearly showed that the silence in expression of BjFAD2-b indeed affected the total expression level of FAD2 gene in CQBJ.

Microsomal ω-6 Oleic Acid Desaturase Enzyme Activity

To test if the decreased total level in transcription of BjFAD2 gene affects the microsomal ω-6 oleate desaturase activity, we measured ω-6 oleate desaturase enzyme activity in vitro. For this purpose, we isolated using microsomal membranes from developing siliques as crude enzyme source according the protocols described previously (Griffiths et al., Biochem. J. 252: 641-647, 1988). This protocol was designed to use the endogenous oleic acid as substrate, and measure the decrease of oleic acid after in vitro incubation. Fatty acid analysis was described as in example 1. Before in vitro incubation in the presence of NADH, the CQBJ microsomal membranes showed significantly higher oleic acid and lower linoleic acid compared to those of WTBJ (Table 2), which suggests lower ω-6 oleate desaturase enzyme activity in CQBJ than in WTBJ. After 50-min in vitro incubation, in the CQBJ microsomal membranes, there was a significant decrease in the content of oleic acid and corresponding increases in the content of linoleic acid and linolenic acid. In contrast, after 50-min in vitro incubation of WTBJ microsomal membranes, the fatty acid profile was unchanged. This probably reflects the achievement of equilibrium between substrate and product of the microsomal ω-6 oleic acid desaturase enzyme before in vitro incubation in wild type microsomal membranes. This also suggests that the ω-6 oleic acid desaturase activity is higher in WTBJ than that in CQBJ. It is noteworthy that after 50-min in vitro incubation, the content of oleic acid in CQBJ was lower than that of WTBJ and the linolenic acid in CQBJ was higher than that of WTBJ. This is probably due to the up regulation of linoleic $\Delta^{15}$-desaturase (BjFAD3) as demonstrated by RT-PCR (data not shown).

TABLE 2

Assay for Microsomal ω-6 Oleic Acid Desaturase Activity in WTBJ and CQBJ

| | WTBJ | | CQBJ | |
|---|---|---|---|---|
| Fatty Acids[a] | 0 min | 50 min | 0 min | 50 min |
| C16:0 | 18.05 | 18.10 | 15.55 | 18.90 |
| C18:0 | 4.95 | 5.00 | 4.70 | 5.00 |
| C18:1 | 7.70 | 7.95 | 16.05 | 3.50 |
| C18:2 | 37.20 | 37.00 | 25.40 | 32.45 |
| C18:3 | 28.95 | 28.80 | 28.45 | 36.15 |
| C20:1 | 0.29 | 0.41 | 1.19 | 0.45 |
| C22:1 | ND | ND | 3.79 | 0.16 |

[a]Values are given as mole percentage and represent the average of two separate experiments.
ND, not detectable.

Example 4

Cloning of the Upstream Non-Coding Regions of BjFAD2-a and BjFAD2-b Genes

To elucidate how the BjFAD2-b gene expression is silenced in CQBJ, we decided to characterize the upstream regulatory region of the BjFAD2-b gene. We used a TOPO® Walker Kit (Version G; Invitrogen) to amplify the upstream non-coding region of the BjFAD2-b gene according to the manufacturer's protocols with minor modifications. All reagents used in this experiment were included in the kit unless specified otherwise. The key reagent of the TOPO® Walker Kit is the TOPO® linker, a 58 bp double-stranded DNA oligonucleotide that has Vaccinia virus topoisomerase I covalently attached to a single 3' T-overhang at one end. It contains two primer-binding sites: LinkAmp primer 1 is for the first PCR and LinkAmp primer 2 is for the nested PCR. The reverse primers were designed based on the ORF sequences of BjFAD2-a and BjFAD2-b genes as follows: 2BR correspond to nucleotide positions 80-101 of the BjFAD2-b; 2BR3 corresponds to nucleotide positions 61-80 of the BjFAD2-b; 2BR4 corresponds to nucleotide positions 50-71 of both BjFAD2-a and BjFAD2-b. Although 2BR4 corresponds to both BjFAD2-a and BjFAD2-b, the final PCR product from this TOPO® Walker Kit is expected to be the BjFAD2-b only because 2BR and 2BR3 are BjFAD2-b gene specific.

Genomic DNA was isolated from leaf tissue of WTBJ and CQBJ as described previously (Dellaporta et al., Plant Mol. Biol. Rep. 1: 19-21,1983). After digesting with the restriction enzyme, PstI, the genomic DNA was de-phosphorylated with calf intestinal alkaline phosphatase (CIAP). For primer extension, 125 ng of cut and de-phosphorylated genomic DNA was primed with the reverse primer, 2BR (SEQ ID NO: 7) in a total volume of 20 μl containing 2 μl of 10×Taq PCR buffer minus $MgCl_2$ and 2 units of Taq DNA polymerase (BRL), 1.5 mM $MgCl_2$, 0.25 μM 2BR primer, and 50 μM of each dNTP. After the DNA template was heat denatured at 94° C. for 4 min and primer annealed at 58° C. for 1 min, the extension reaction was performed for 20 min at 72° C. After extension the mixture was immediately chilled on ice and then 4 μl of the extended DNA was mixed with 1 μl of 10×PCR buffer with $MgCl_2$ (Invitrogen), 4 μl $dH_2O$ and 1 μl of the TOPO® linker. This mixture was incubated at 37° C. for 5 min for ligation.

After ligation of the extended DNA to the TOPO® linker, two PCR reactions were performed to amplify the upstream region of the BjFAD2-b gene. The first PCR was performed in a total volume of 20 μl containing 1 μl of the above ligation mixture, 2 μl of 10×Taq DNA polymerase buffer with $MgCl_2$ (Invitrogen) and 2 units of Taq DNA polymerase (BRL), 0.25 μM primer 2BR3 (SEQ ID NO: 8), 50 ng AmpLinker primer 1 and 50 μM of each dNTP. The amplification was done with 35 cycles of 1 min at 94° C., 1 min at 56.5° C. and 2 min at 72° C. The nested PCR was performed in a total volume of 20 μl containing 1 μl of a 0.1 dilution of the first PCR product, 2 μl of 10×Taq DNA polymerase buffer minus $MgCl_2$ and 2 units of Taq DNA polymerase (BRL), 0.25 μM primer 2BR4 (SEQ ID NO: 9), 50 ng AmpLinker primer 2, 1.5 μM $MgCl_2$, and 50 μM of each dNTP. The amplification was done with 35 cycles of 1 min at 94° C., 1 min at 58° C., and 2 min at 72° C. Both PCR reactions were incubated at 94° C. for 5 min and 72° C. for 10 min before and after cycling respectively.

Figure 5:
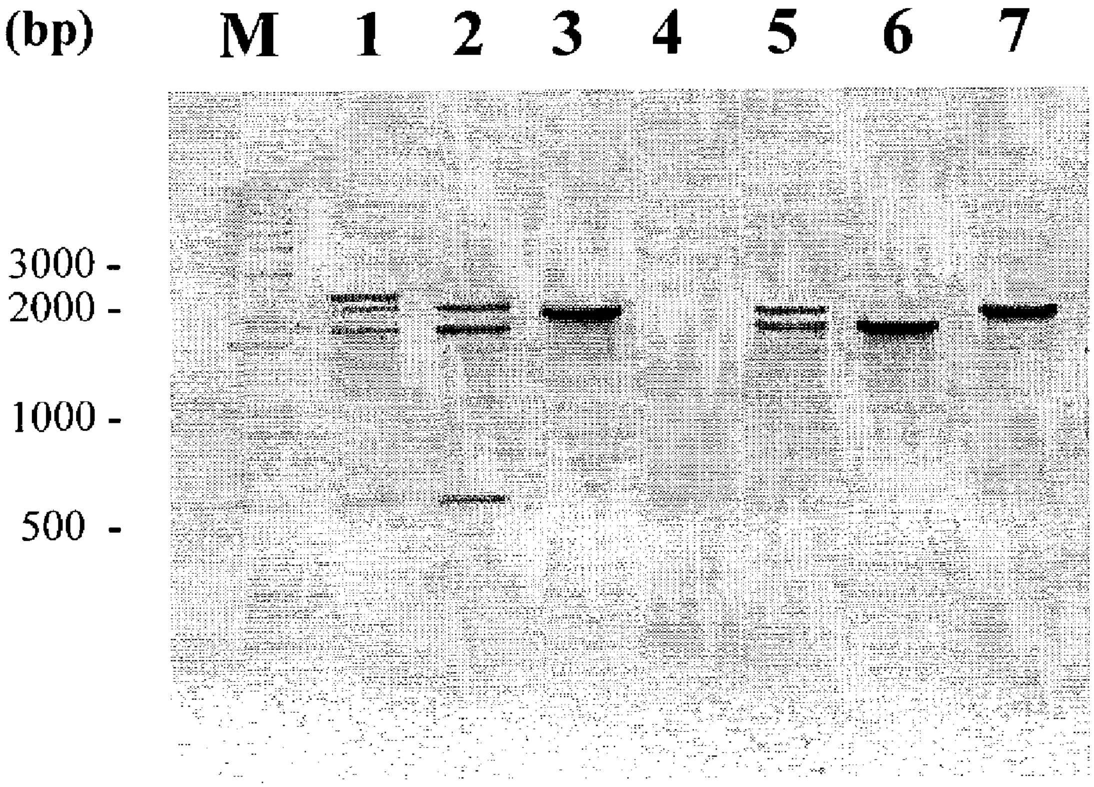
FIG. 5 shows results from direct PCR amplification of the BjFAD2 genes. PCR amplification of the BjFAD2 genes was performed using leaf DNA as template with the following primer pairs: FD2Pup-1+2BR2 (lanes 1 and 2); FD2Pup-1+2BR5 (lanes 3 and 4); FD2Pup-1+2BR4 (lanes 5 and 6). Genomic DNA was isolated either from WTBJ (Lanes 1, 3, and 5) or CQBJ (Lanes 2, 4, and 6). Lane 7 is the result of nested PCR using the DNA walker Kit. M: 1 Kb plus DNA size marker (BRL).

The PCR products were electrophoresed on a 1% agarose gel in TAE running buffer with the 1 Kb plus DNA ladder (BRL) as DNA size marker. A single fragment of ~2100 bp was amplified form WTBJ (FIG. 5, lane 7). However, no amplification product was detected from CQBJ. The same results were obtained when the experiment was repeated twice. In order to obtain sequence information, the ~2100 bp DNA fragment amplified from WTBJ was excised from the agarose gel and purified using the Geneclean II Kit (Bio101), which was cloned into a TA cloning vector (TOPO pCR3.9, Invitrogen). Two randomly selected colonies were used for isolating plasmid DNA. The insert DNA was sequenced completely from both ends. The 3' end sequence (71 bp) is 100% identical to the BjFAD2-b ORF, which confirms that this ~2100 bp fragment is indeed the BjFAD2-b gene.

The 5' end sequence of this ~2100 bp fragment was used to design two forward primers FAD2Pup-1 (SEQ ID NO: 10) and FAD2Pup-2 (SEQ ID NO: 11) in order to amplify the BjFAD2-b gene by direct genomic PCR. For direct genomic PCR, 100 ng of genomic DNA was used as template in total volume of 50 ul. Other PCR conditions and cycling parameters were the same as used for the nested PCR described above. When primer pair FAD2Pup-1 and 2BR4 was used in PCR, two fragments were amplified from WTBJ (FIG. 5 lane 5). The top fragment is identical in size to the fragment amplified by the TOPO® Walker Kit (FIG. 5, lane 7), which indicated that the top fragment of WTBJ is the BjFAD2-b gene. The second fragment is approximately 200 bp smaller than the top fragment. Using the same primer pair, only one fragment was amplified from CQBJ (FIG. 5, lane 6), which is identical in size to the second fragment of the WTBJ (FIG. 5, lane 5). The results suggest that the BjFAD2-b gene is missing from the CQBJ genome.

Co-amplification of the second fragment from the WTBJ suggests that it may represent another member of the BjFAD2 gene family, probably the BjFAD2-a gene, which shares sequence similarity with the BjFAD2-b gene. In fact, when primer FAD2Pup-2, which is 40 bp upstream of primer FAD2Pup-1, was paired with primer 2BR4, identical amplification patterns were obtained. Specifically, two fragments were amplified from WTBJ and only one fragment was amplified from CQBJ (data not shown). The result indicates that the two fragments also share sequence homology in their upstream non-coding regions.

To obtain sequence information of the two fragments, another reverse primer 2BR2 (SEQ ID NO: 12) that corresponds to the nucleotide positions 430-450 of ORF for both BjFAD2-a and BjFAD2-b was designed. Direct genomic PCR was performed with the primer pair FAD2Pup-1 and 2BR2. This would allow amplification of the BjFAD2 genes plus longer ORF sequences so that BjFAD2-a and BjFAD2-b could be easily identified. PCR conditions and cycling parameters are the same as described above. As a result, three fragments were amplified from WTBJ, which were ~2400 bp, ~2100 bp and ~1800 bp in size, respectively (FIG. 5, lane 1). Two fragments were amplified from CQBJ (FIG. 5 lane 2), which are identical to the second and third fragment of the WTBJ, respectively (FIG. 5 lane 1). The results are consistence with the notion that the BjFAD2-b gene is deleted from the CQBJ genome.

All three fragments were excised and purified from the agarose gel. Then each of the three fragments was cloned into a TA cloning vector (TOPO pCR3.9, Invitrogen) according to the protocols described above. The inserts were completely sequenced. The sequence of the top fragment is shown in FIG. 6B (SEQ ID NO: 14). It is 2408 bp in length that includes 450 bp fragment identical to BjFAD2-b ORF sequence, confirming it is the BjFAD2-b gene. The sequence of the second fragment is shown in FIG. 6A (SEQ ID NO: 13). It consists 2166 bp that includes a 450 bp fragment identical to the BjFAD2-a ORF sequence, which confirms that it is the BjFAD2-a gene. The upstream non-coding sequence of BjFAD2-b gene contains a perfect TATA box in positions of 1003-1010 bp. The upstream non-coding sequence of BjFAD2-a gene also contains a perfect TATA box sequence in positions of 1023-1030 bp. Sequence analysis of the non-coding regions indicated that they share 81.9% nucleotide sequence identity. The high sequence similarity in the non-coding regions of BjFAD2-b and BjFAD2-a explains the fact that both primers FAD2Pup-1 and FAD2Pup-2 can simultaneously amplify BjFAD2-a and BjFAD2-b genes from WTBJ when paired with primer 2BR4 (FIG. 5, lane 5) or 2BR2 (FIG. 5, lane 1).

The third fragment consists 1810 bp that includes 435 bp fragment that shares similarity to both BjFAD2-a and BjFAD2-b ORF sequences. This 435 bp fragment shares 83.9% and 81.7% nucleotide sequence identity with the BjFAD2-a and BjFAD2-b ORF sequences, respectively. This putative coding sequence contains a 15-bp deletion when compared to the ORFs of BjFAD2-a and BjFAD2-b. In addition, it also contains an in-frame stop codon. The sequence of the non-coding region of the third fragment shares 49.4% and 62.8% nucleotide sequence identity, respectively, with BjFAD2-a and BjFAD2-b non-coding regions. It is likely that this fragment represents another member of FAD2 gene family in *B. juncea* genome. However, it does not code functional FAD2 and has become silenced in gene expression, which is consistent with the fact that it could not be amplified by RT-PCR.

Example 5

Allelic Variation of BjFAD2-b Gene in WTBJ and CQBJ

Figure 7:
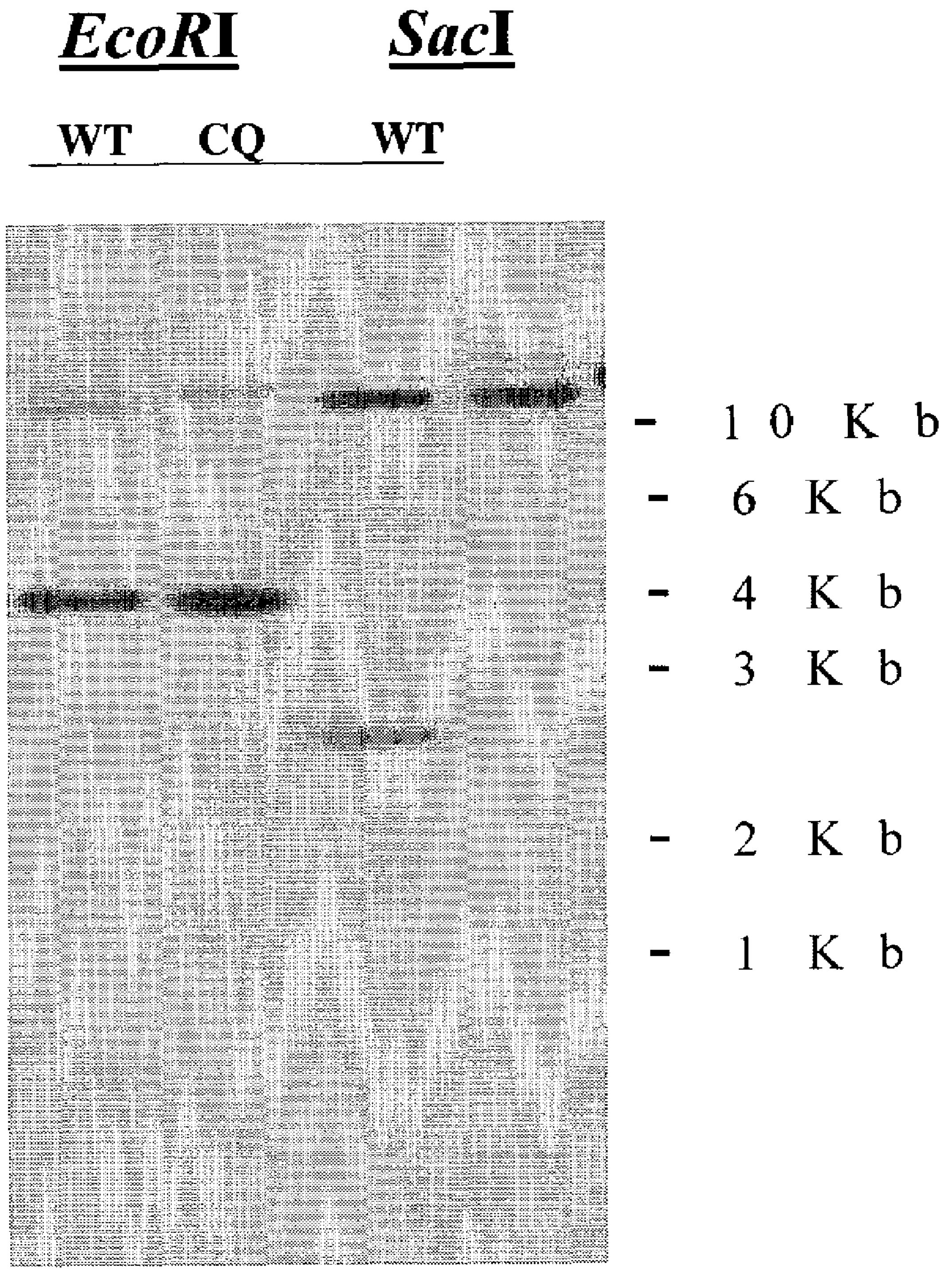
FIG. 7 shows a Southern blot analysis of the BjFAD2 gene. Leaf genomic DNA (25 μg) from WTBJ and CQBJ were digested with the indicated enzymes, separated by agarose gel electrophoresis, and transferred to a nylon membrane, which was hybridized to [$^{32}$P]-dATP-labeled BjFAD2-a cDNA probe. DNA fragment sizes are indicated.

FIG. 7 shows the results of a genomic Southern blot, which was designed to determine the BjFAD2 gene copy numbers in the *B. juncea* genome. For this purpose, 25 ug of total genomic DNA from leaf tissues of both WTBJ and CQBJ were digested with restriction enzymes EcoRI and SacI. After electrophoreses on a 0.8% agarose gel the separated genomic DNA fragments were blotted on nylon membrane and hybridized with the [α-$^{32}$P]-dCTP labeled BjFAD2-a CDNA probe under the conditions of high stringency. Probe was prepared in a same way as for Northern blot experiment, which was described in example 3.

As shown in FIG. 7, There are three fragments hybridized to BjFAD2-a probe from the EcoRI digested WTBJ genomic DNA. However, only two fragments hybridized to BjFAD2-a probe from the EcoRI digested CQBJ genomic DNA. After SacI digestion the WTBJ genomic DNA generated two hybridization bands. But only one hybridization band was detected from the SacI digested CQBJ genomic DNA. The results indicated that there is indeed one BjFAD2 member missing from the CQBJ genome. This, together with the experimental data from RT-PCR and direct genomic PCR, confirms that the BjFAD2-b gene is deleted from the CQBJ genome.

Example 6

Use of the BjFAD2-b Gene Information in High Oleic Acid Breeding

The sequence information of BjFAD2-b and the fact it is deleted from the CQBJ genome make it possible that the BjFAD2-b can be used as a gene tag for high oleic acid *B. juncea* breeding. When the primer FAD2Pup-1 is combined with reverse primer 2BR2 or primer 2BR4 in genomic PCR, BjFAD2-a gene can be amplified from both WTBJ and CQBJ (FIG. 5, lanes 1, 2, 5 and 6). However, BjFAD2-b gene can be amplified only from the WTBJ (FIG. 5, top fragment of lane 1, and top fragment of lane 5). We have designed another reverse primer 2BR5 (SEQ ID NO: 15), which corresponds to the positions of 24-47 bp of BjFAD2-b ORF specifically. 2BR5 would allow specific amplification of BjFAD2-b.

When the primer FAD2Pup-1 is combined with primer 2BR5 in genomic PCR, only the BjFAD2-b was amplified from WTBJ (FIG. 5, lane 3), indicating that primer 2BR5 is specific for BjFAD2-b. As expected, this primer pair failed to produce any amplification product from CQBJ (FIG. 5, lane 4). The PCR results obtained from this primer pair not only confirm the fact that the BjFAD2-b gene is deleted from the CQBJ genome, but also indicate that the BjFAD2-b allelic variation can be used as a gene tag in plant breeding, used as in breeding new lines of *B. juncea*, for selection of the high oleic acid trait.

Table 3 shows the results of PCR screening for the high oleic acid trait using the BjFAD2-b and BjFAD2-a genes as markers in a collection of breeding lines. These lines were produced through the doubled haploid techniques and are therefore homozygous. Leaf genomic DNAs were used for PCR screening and the mature seeds produced from each self-pollinated individual plant were used for fatty acid analysis. Table 3 includes only the lines screened by both primer pairs. There were more lines screened by either primer pair "FAD2Pup-1+2BR4" or primer pair "FAD2Pup-1+2BR5". No discrepancy was found for a total of 59 lines screened. The results indicated that each primer pair alone may be used for screening.

TABLE 3

PCR screening for oleic acid trait in *B. juncea* lines.

| | AMPLIFICATION PRODUCTS BY PCR* | | Oleic |
|---|---|---|---|
| *B. junea* Lines | FAD2Pup-1 + 2BR4 | FAD2Pup-1 + 2BR5 | Acid Content |
| J96D-0899 | 1 | 0 | High |
| J97D-3285 | 1 | 0 | High |
| J98D-1384 | 1 | 0 | High |
| J98D-2049 | 1 | 0 | High |
| J99D-3298 | 1 | 0 | High |
| J00D-00591 | 1 | 0 | High |
| J00D-01180 | 1 | 0 | High |
| J00D-01202 | 1 | 0 | High |
| J00D-13396 | 1 | 0 | High |
| J00D-13495 | 1 | 0 | High |
| J00D-13665 | 1 | 0 | High |
| J00D-13694 | 1 | 0 | High |
| J00D-01976 | 1 | 0 | High |
| J00D-06074 | 1 | 0 | High |
| J92D-1356 | 2 | 1 | Low |
| J98D-8124 | 2 | 1 | Low |
| J99D-8400 | 2 | 1 | Low |
| J98D-11194 | 2 | 1 | Low |
| J00D-2309 | 2 | 1 | Low |
| J00D-01823 | 2 | 1 | Low |
| J00D-05875 | 2 | 1 | Low |
| J00D-02421 | 2 | 1 | Low |
| J00D02169 | 2 | 1 | Low |
| J00D-03055 | 2 | 1 | Low |

*The number of amplification products by each primer pair is indicated. For the primer pair FAD2Pup-1 + 2BR4, 1 indicates the amplification of BjFAD2-a only and 2 indicates the amplifications of both BiFAD2-a and BiFAD2-b. For primer pair FAD2Pup-1 + 2BR5, 0 and 1 indicate the absence and presence of BjFAD2-b, respectively. J96D-0899 (representative CQBJ) and J92D-1356 (representative WTBJ) are included. High, ~60% oleic acid; Low, ~45% oleic acid.

REFERENCES

The following documents are specifically incorporated herein by reference.

Agnihotri, A., Kaushik, N., Singh, N. K., Raney, J. P. and Downey, R. K. 1995. Selection for better agrononical and nutritional characteristics in Indian rapeseed-mustard. Proc. 9.sup.th Int. Rapeseed Cong., Cambridge, U.K. Vol. 2:425-427.

Ames, B. N. 1983. Dietary carcinogens and anticarcinogens. Science 221:1256-1264.

Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.

Downey, R. K. and Rakow, G. F. W. 1987. Rapeseed and mustard. In: Principles of cultivar development. W. R. Fehr, ed. Macmillian, N.Y. Pp. 437-486.

Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081-1084.

Food Chemicals Codex. 1996. 4.sup.th Edition. Committee on Food Chemicals Codex, Food and Nutrition Board, Institute of Medicine, National Academy of Sciences. National Academy Press, Washington. pp. 77-79.

Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.

Love, H. K., Rakow, G., Raney, J. P. and Downey, R. K. 1990. Development of low glucosinolate mustard. Can. J. Plant Sci. 70:419-424.

Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. Vol. 1:164-169.

McDonald, B. E. 1995. Oil properties of importance in human nutrition. In: Brassica Oilseeds: Production and Utilization. D. S. Kimber and D. I. McGregor, eds., CAB International, Oxon, U.K., pp. 291-299.

Potts et al., 1999. Canola-quality *Brassica juncea*, a new oilseed crop for the Canadian prairies. The proceedings of 10th International Rapeseed Congress in Sep. 26-29, 1999; Canberra, Australia; CD-ROM.

Potts and Males. 1999. Inheritance of fatty acid composition in *Brassica juncea*. The proceedings of 10th International Rapeseed Congress in Sep. 26-29, 1999; Canberra, Australia; CD-ROM.

Rakow, G. 1991. Canola quality mustard. Proc. Special Cropportunities I: A conference organized by the Crop Development Centre and the Extension Division, University of Saskatchewan, Saskatoon, Canada pp. 55-59.

Rakow, G., Raney, J. P. and Males, D. 1995. Field performance of canola quality *Brassica juncea* Proc. 9.sup.th Int. Rapeseed Congress, Cambridge, U.K. Vol. 2:428-430.

Raney, P., Rakow, G. and Olson, T. 1995. Development of zero erucic, low linolenic *Brassica juncea* utilizing interspecific crossing. Proc. 9.sup.th Int. Rapeseed Congress, Cambridge, U.K. Vol. 2:413-415.

Stotjesdijk et al., 1999. Genetic manipulation for altered oil quality in Brassica. The proceedings of 10th International Rapeseed Congress in Sep. 26-29, 1999; Canberra, Australia; CD-ROM.

Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7:83-87.

Swanson, E. B., Herrgesell, M. J., Arnoldo, M., Sippell, D. W. and Wong, R. S. C. 1989. Microspore mutagenesis and selection: canola plants with field tolerance to the imidazolinones. Theor. Appl. Genet. 78:525-530.

Thiagarajah, M. R. and Stringham, G. R. 1993. A comparison of genetic segregation in traditional and microspore-derived populations of *Brassica juncea* L. Czern and Coss. Plant Breeding 111:330-334.

Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning.

As used herein, the term "allele" is used in its normal sense, to refer to alternative forms of a genetic locus. A "locus" is the position on a chromosome of a gene or other chromosome marker. As used herein, the term "locus" is not restricted to mean only regions of DNA that are expressed.

Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

Deposit Information

A deposit of the Saskatchewan Wheat Pool, Inc. proprietary *Brassica juncea* line J96D-0899 disclosed above and recited in the appended claims has been made with the American Type Culture Collection (ATCC), 10801 University Boulevard, Manassas, Va. 20110. The date of deposit was Oct. 27, 2006. The deposit of 2,500 seeds was taken from the same deposit maintained by Saskatchewan Wheat Pool, Inc. since prior to the filing date of this application. All restrictions upon the deposit have been removed, and the deposit is intended to meet all of the requirements of 37 C.F.R. 1.801-1.809. The ATCC accession number is PTA-7954. The deposit will be maintained in the depository for a period of 30 years, or 5 years after the last request, or for the effective life of the patent, whichever is longer, and will be replaced as necessary during that period.

What is claimed is:

1. A *Brassica juncea* plant having a tetraploid genome selected to have only two expressible FAD2 coding sequences, wherein the plant is capable of producing an oilseed bearing an endogenous oil having an oleic acid content of at least 55% by weight, an erucic acid content of less than 1% by weight, wherein the plant is the progeny of Brassica juncea parent line J96D-0899, deposited as ATCC Accession No. PTA-7954, and wherein the expressible FAD2 coding sequences are homologous to the BjFAD2-a coding sequence and have an open reading frame with at least 95% identity to SEQ ID NO: 3 and wherein the BjFAD2-b loci coding sequence with SEQ ID NO:5 has been deleted.

2. A *Brassica juncea* plant having a tetraploid genome selected to have only two expressible FAD2 coding sequences, wherein the plant is recombinant for at least one expressible FAD2 coding sequence, wherein the plant is capable of producing an oilseed bearing an endogenous oil having an oleic acid content of at least 55% by weight, an erucic acid content of less than 1% by weight, wherein the plant is not the progeny of Brassica juncea parent lines J90-3450 and J90-4316 deposited respectively as ATCC Accession Nos. 203389 and 203390 but is the progeny of Brassica juncea parent line J96D-0899, deposited as ATCC Accession No. PTA-7954, and wherein the expressible FAD2 coding sequences are homologous to BjFAD2-a coding sequence and have an open reading frame with at least 95% identity to SEQ ID NO:3 and wherein the BjFAD2-b loci coding sequence with SEQ ID NO:5 has been deleted.

* * * * *

SEQUENCE LISTING

```
<160> NUMBER OF SEQ ID NOS: 17

<210> SEQ ID NO 1
<211> LENGTH: 22
<212> TYPE: DNA
<213> ORGANISM: Brassica juncea

<400> SEQUENCE: 1

caatgggtgc aggtggaaga at                                            22


<210> SEQ ID NO 2
<211> LENGTH: 22
<212> TYPE: DNA
<213> ORGANISM: Brassica juncea
```

-continued

<400> SEQUENCE: 2

```
tcataactta ttgttgtacc ag                                           22
```

<210> SEQ ID NO 3
<211> LENGTH: 1156
<212> TYPE: DNA
<213> ORGANISM: Brassica juncea

<400> SEQUENCE: 3

```
satgggtgca ggtggaagaa tgcaagtgtc tcctccctcg aagaagtctg aaaccgacac     60

catcaagcgc gtaccctgcg agacaccgcc cttcactgtc ggagaactca agaaagcaat    120

cccaccgcac tgtttcaaac gctcgatccc tcgctctttc tcctacctca tctgggacat    180

catcatagcc tcctgcttct actacgtcgc caccacttac ttccctctcc tccctcaccc    240

tctctcctac ttcgcctggc ctctctactg ggcctgccag ggctgcgtcc taaccggcgt    300

ctgggtcata gcccacgagt gcggccacca cgccttcagc gactaccagt ggcttgacga    360

caccgtcggt ctcatcttcc actccttcct cctcgtccct tacttctcct ggaagtacag    420

tcatcgacgc caccattcca acactggctc cctcgagaga gacgaagtgt ttgtccccaa    480

gaagaagtca gacatcaagt ggtacggcaa gtacctcaac aaccctttgg gacgcaccgt    540

gatgttaacg gttcagttca ctctcggctg gcctttgtac ttagccttca acgtctcggg    600

aagaccttac gacggcggct tcgcttgcca tttccaccct aacgctccca tctacaacga    660

ccgcgagcgt ctccagatat acatctccga cgctggcatc ctcgccgtct gctacggtct    720

ctaccgctac gctgctgtcc aaggagttgc ctcgatggtc tgcttctacg gagtcccgct    780

tctgatagtc aacgggttct tagttttgat cacttacttg cagcacacgc atccttccct    840

gcctcactac gattcgtctg agtgggattg gttgaggga gcgttggcta ccgttgacag    900

agactacggg atcttgaaca aggtcttcca caatatcacg gacacgcacg tggcgcatca    960

cctgttctcg accatgccgc attatcacgc gatggaagct accaaggcga taaagccgat   1020

actgggagag tattatcagt tcgatgggac gccggtggtt aaggcgatgt ggagggaggc   1080

gaaggagtgt atctatgtgg aaccggacag gcaaggtgag aagaaaggtg tgttctggta   1140

caacaataag ttatga                                                  1156
```

<210> SEQ ID NO 4
<211> LENGTH: 384
<212> TYPE: PRT
<213> ORGANISM: Brassica juncea

<400> SEQUENCE: 4

```
Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95
```

-continued

```
Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

<210> SEQ ID NO 5
<211> LENGTH: 1155
<212> TYPE: DNA
<213> ORGANISM: Brassica juncea

<400> SEQUENCE: 5

```
atgggtgcag gtggaagaat gcaggtttct ccttctccca agaagtccga aaccgatacc      60

ctcaagcgtg ttccctgcga gacgcctccc ttcacagtag gagagctcaa gaaagccatc     120

ccaccgcact gtttcaaacg ctccatccct cgctccttct cctacctcat ctgggacatc     180

atcgtagcct cctgcttcta ctacgtcgcc accacctact ttcccctcct ccctcaccct     240

ctctcttaca ttgcttggcc tctctactgg gcctgccaag gctgcgtcct aaccggcgtc     300

tgggtcatag cccacgaatg cggccaccac gctttcagcg actaccagtg gctagacgac     360

accgtcggtc tcatcttcca ttccttcctc ctcgtccctt acttctcctg gaagtacagt     420

caccgccgtc accattccaa caccggctcg ctcgagagag acgaggtgtt tgtccccaag     480

aaaaaatcag acatcaagtg gtacggcaag tacctcaaca accctctcgg acgcaccgtg     540
```

-continued

```
atgctaaccg tccagttcac tctcggctgg cccttgtact tggccttcaa cgtctcgggc    600

agaccttacc ccgaggggtt cgcctgccat ttccacccga acgctcccat ctacaacgac    660

cgcgaacgcc tccagatata cgtctccgac gctggtatcc tcgccgtctg ttacggtctc    720

taccgttacg cggccgcgca gggagtggcc tcgatggtct gcctctacgg agttccgctt    780

ctgatagtca acgcgttcct cgtcttgatc acttacttgc agcacactca tccttcgttg    840

cctcactacg actcctctga gtgggattgg ttgaggggag ctttggctac cgttgacaga    900

gactacggaa tcttgaacaa ggtcttccac aacatcacgg acacgcacgt ggcgcatcat    960

ctgttctcca cgatgccgca ttatcacgcg atggaggcca cgaaggccat aaagccgata   1020

ctgggagact attaccagtt cgatgggaca ccatgggtta aggcgatgtg gagggaggcg   1080

aaggagtgta tctatgttga accggacagg caaggtgaga agaaaggtgt gttctggtac   1140

aacaataagt tatga                                                    1155


<210> SEQ ID NO 6
<211> LENGTH: 384
<212> TYPE: PRT
<213> ORGANISM: Brassica juncea

<400> SEQUENCE: 6

Met Gly Ala Gly Gly Arg Met Gln Phe Ser Pro Ser Pro Lys Lys Ser
1               5                   10                  15

Glu Thr Asp Thr Leu Lys Arg Phe Pro Cys Glu Thr Pro Pro Phe Thr
            20                  25                  30

Phe Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Phe Ala Ser
    50                  55                  60

Cys Phe Tyr Tyr Phe Ala Thr Thr Tyr Phe Pro Leu Leu Pro His Pro
65                  70                  75                  80

Leu Ser Tyr Ile Ala Trp Pro Leu Tyr Trp Ala Cys Gln Gly Cys Phe
                85                  90                  95

Leu Thr Gly Phe Trp Phe Ile Ala His Glu Cys Gly His His Ala Phe
            100                 105                 110

Ser Asp Tyr Gln Trp Leu Asp Asp Thr Phe Gly Leu Ile Phe His Ser
        115                 120                 125

Phe Leu Leu Phe Pro Tyr Phe Ser Trp Lys Tyr Ser His Arg Arg His
    130                 135                 140

His Ser Asn Thr Gly Ser Leu Glu Arg Asp Glu Phe Phe Phe Pro Lys
145                 150                 155                 160

Lys Lys Ser Asp Ile Lys Trp Tyr Gly Lys Tyr Leu Asn Asn Pro Leu
                165                 170                 175

Gly Arg Thr Phe Met Leu Thr Phe Gln Phe Thr Leu Gly Trp Pro Leu
            180                 185                 190

Tyr Leu Ala Phe Asn Phe Ser Gly Arg Pro Tyr Pro Glu Gly Phe Ala
        195                 200                 205

Cys His Phe His Pro Asn Ala Pro Ile Tyr Asn Asp Arg Glu Arg Leu
    210                 215                 220

Gln Ile Tyr Phe Ser Asp Ala Gly Ile Leu Ala Phe Cys Tyr Gly Leu
225                 230                 235                 240

Tyr Arg Tyr Ala Ala Ala Gln Gly Phe Ala Ser Met Phe Cys Leu Tyr
                245                 250                 255
```

-continued

```
Gly Phe Pro Leu Leu Ile Phe Asn Ala Phe Leu Phe Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Phe Asp Arg Asp Tyr Gly Ile
    290                 295                 300

Leu Asn Lys Phe Phe His Asn Ile Thr Asp Thr His Phe Ala His His
305                 310                 315                 320

Leu Phe Ser Thr Met Pro His Tyr His Ala Met Glu Ala Thr Lys Ala
                325                 330                 335

Ile Lys Pro Ile Leu Gly Asp Tyr Tyr Gln Phe Asp Gly Thr Pro Trp
            340                 345                 350

Phe Lys Ala Met Trp Arg Glu Ala Lys Glu Cys Ile Tyr Phe Glu Pro
        355                 360                 365

Asp Arg Gln Gly Glu Lys Lys Gly Phe Phe Trp Tyr Asn Asn Lys Leu
    370                 375                 380


<210> SEQ ID NO 7
<211> LENGTH: 22
<212> TYPE: DNA
<213> ORGANISM: Brassica juncea

<400> SEQUENCE: 7

cctactgtga agggaggcgt ct                                              22


<210> SEQ ID NO 8
<211> LENGTH: 20
<212> TYPE: DNA
<213> ORGANISM: Brassica juncea

<400> SEQUENCE: 8

tcgcagggaa cacgcttgag                                                 20


<210> SEQ ID NO 9
<211> LENGTH: 23
<212> TYPE: DNA
<213> ORGANISM: Brassica juncea

<400> SEQUENCE: 9

acacgcttga gggtatcggt ttc                                             23


<210> SEQ ID NO 10
<211> LENGTH: 23
<212> TYPE: DNA
<213> ORGANISM: Brassica juncea

<400> SEQUENCE: 10

gaagccaagc acgatcctcc att                                             23


<210> SEQ ID NO 11
<211> LENGTH: 33
<212> TYPE: DNA
<213> ORGANISM: Brassica juncea

<400> SEQUENCE: 11

gatattttt taagtttttt tctcacatgg gag                                   33


<210> SEQ ID NO 12
<211> LENGTH: 21
<212> TYPE: DNA
<213> ORGANISM: Brassica juncea
```

-continued

<400> SEQUENCE: 12
cgagccggtg ttggaatggt g 21

<210> SEQ ID NO 13
<211> LENGTH: 2166
<212> TYPE: DNA
<213> ORGANISM: Brassica juncea

<400> SEQUENCE: 13
gaagccaagc acgatcctcc attctcaact ttatagcatt tttttctttt ctttccggct 60
accactaact tctacagttc tacttgtgag tcggcaagga cgtttcctca tattaaagta 120
aagacatcaa ataccataat cttaatgcta attaacgtaa cggatgagtt ctataacaca 180
acccaaacta gtctttgtga acattaggat tgggtaaacc aatatttaca ttttaaaaac 240
aaaatacaaa aagaaacgtg ataaacttta taaaagcaat tatatgatca cggcatcttt 300
ttcacttttc cgtaaatata tataagtggt gtaaatatca gatatttgga gtagaaaaaa 360
aaaaaaaaaa aaaagaaata tgaagagagg aaataatgga ggggcccact agtaaaaaag 420
aaagaaaaga gatgtcactc aatcgtctca cacgggcccc cgtcaattta aacggcctgc 480
cttctgccca atcgcatctt accagaacca gagagattca ttaccaaaga gatagagaga 540
gaaagagagg agacagagag agtttgagga ggtgcttctt cgtagggttc atcgttatta 600
acgttaaatc ttcatccccc tacgtcaacc agctcaaggt ccctttcttc ttccatttcc 660
tctcattttt acgttgtttt caatcttggt ctgttctttt cttatcgctt ttctattcta 720
tctatcattt ttgcttttca gtcgatttaa ttctagacct gttaatattt attgcattaa 780
actatagatc tgttcttgat tctctgtttt cttgtgtgaa atcttgatgc tgtctttacc 840
attaatctga ttatattgtc tataccttgg agaatatgaa atgttgcatt ttcatttgtc 900
cgaatacaaa ctgtttgact ttcaatcttt tttaatgatt tattttgatg ggttggtgga 960
gttgaaaaat caccatagca gtctcacgtc ctggtcttag aaatatcctt cctattcaaa 1020
gttatatata tttgtttact tgtcttagat ctggacctga gacatgtaag tacctatttg 1080
ttgaatcttt gggtaaaaaa cttatgtctc tgggtaaaat ttgcttggag atttgaccga 1140
ttcctattgg ctcttgattc tgtaattacg taatacatga aaaatgtttc atttggccta 1200
tgctcacttc atgcttataa actttttctt gcaaattaat tggattagat gctccttcat 1260
agattcagat gcaatagatt tgcatgaaga aaataataga attcatgata gtaaaaagat 1320
tgtatttttg tttgtttgtt tatgtttaaa agtctatatg ttgacaatag agttgctatc 1380
aactgtttca tttagtttat gtttttgtca agttgcttat tctaagagac attgtgatta 1440
tgacttgtct tctctaacgt agtttagtaa taaaagacga aagaaattga tatccacaag 1500
aaagagatgt aagctgtaac gtatcaaatc tcattaataa ctagtagtat tctcaacgct 1560
atcgtttatt tctttctttg gtttgccact atatgccgct tctctcctct tttgtcccac 1620
gtactatcca ttttttgaa actttaataa cgtaacactg aatattaatt tgttggttta 1680
attaactttg agtttgtttt tggtttatgc agaaacatgg gtgcaggtgg aagaatgcaa 1740
gtgtctcctc cctcgaagaa gtctgaaacc gacaccatca agcgcgtacc ctgcgagaca 1800
ccgcccttca ctgtcggaga actcaagaaa gcaatcccac cgcactgttt caaacgctcg 1860
atccctcgct ctttctccta cctcatctgg gacatcatca tagcctcctg cttctactac 1920
gtcgccacca cttacttccc tctcctccct caccctctct cctacttcgc ctggcctctc 1980

-continued

```
tactgggcct gccagggctg cgtcctaacc ggcgtctggg tcatagccca cgagtgcggc   2040

caccacgcct tcagcgacta ccagtggctt gacgacaccg tcggtctcat cttccactcc   2100

ttcctcctcg tcccttactt ctcctggaag tacagtcatc gacgccacca ttccaacact   2160

ggctcc                                                              2166


<210> SEQ ID NO 14
<211> LENGTH: 2408
<212> TYPE: DNA
<213> ORGANISM: Brassica juncea

<400> SEQUENCE: 14

gaagccaagc acgatcctcc attctcccac ttttagcatt tctttttttt ttttctttct     60

ttccggctac cacttacttg tacttgtaag tcgagtcggt aagaacgttt cctcatatta    120

aactaaagac atcatatatc gtcgccttga tgctaattaa cgtaaccgat gaaaactgta    180

acagaatcca aaccaatctc tctggatatt tggattacca gtgggtcaac caatatttac    240

ttttttttcag aacgaaacac aaaaggaaac ttgataaact ttataaaagt aaacataaat   300

atattcagta ttcactgcct ctttttctgc ttttccgtaa atacataagt gccgtaaata    360

tcagatattt ggaatagaaa agtaataaag gaaaaaaata tgaggagagg aaaaaaagag    420

gggcccagtt gtaaaaaaaa gagagatgtc cactcaatcc tcttctctct cattctttta    480

cccacgggcc gtcaatttaa acggcctagc ttctgcccca tttgcttctg accagaaacc    540

acagagagag agagagtttc attaccaaag agagagagat aggagagaga agatagagag    600

agtctgcgga ggagcttctt cgtagggttc atcgttatta acgttaaatc tctatccccc    660

tacgtcagcc agctcaaggt ccccttcttc ttcttcttct tccatttctt ctcattttac    720

gtttttatc ttcttcaatc ttttgaacct tttctggtct gtggtaatct tattccctct     780

tatcattttg cgcttcaatc gatttcatta tagatctgac aatattgatt gcattcaact    840

atagatctgg tagcgattct ctgtttccat gttaaaatct gttgctgtct tttactattg    900

ttatggttat tgtctatatc gtcgagtata tgaaatgttg cattttcatt ttgttcaaat    960

acgtaagtgt ttgactatct aatttcgatc gttattttta attatatata ttattgatcg   1020

gttggtagag ttgaaaaaaa ttcaccagaa atattatgcg tagcagcctc accgtcctgg   1080

ttataaaatc atcccatctg tttattcaaa agttatatac tactatttgt ttagatctgg   1140

acctgagtat atgtaaagct gtattatctt tgttaaattt gctcctattt gttgaatctt   1200

tggcagattt gaccgattcc tattcgcttc ttggtactgt aattacatag taaatggaaa   1260

aattttcatt ggctgcgtgt aaaaaaaaaa aaagaagttc cattgactta tgctagaact   1320

caaactcttg ctcataaacc ttttgtagta caaattaatt gaatatgggg taggtaaact   1380

caggaatctt tcatagattc agatgcaaat agagctgcat gtagaaaata ataggattca   1440

tgacagtaaa aagaagattg gtactatgtt ttgtttgttt ctgtttaaaa gtctatatga   1500

ttgacaataa tatttgttgc tctcaaattc tctctactgt ttcatttagc tttttttttt   1560

ttggccaagt tgatatccaa gaggaatagt gattatggct gctatcttaa aaaaatcgat   1620

atccgcaaga aagagatgtg agctgtagcg tatcaaatct tattcattta ctagtcgtat   1680

tctcaacgct atcgtttatt tctttttctt tcttcggttt gccactaaaa gccgcttccc   1740

tgctctttgt tacacttagt atccattttt gtggtagtcc attttttgaa acgtaacatt   1800

gaatgttttg tctgaaaaaa aaaatttgat ggtttaataa attcttattc tcgcatagac   1860

atttgtcagt taagattaat aagtctttag ctttggacat tgagtttcag ctcctgattg   1920
```

-continued

```
aagtctttgc ttttgttttt ttttccttgc agaaaacaat gggtgcaggt ggaagaatgc   1980

aggtttctcc ttctcccaag aagtccgaaa ccgataccct caagcgtgtt ccctgcgaga   2040

cgcctccctt cacagtagga gagctcaaga aagccatccc accgcactgt ttcaaacgct   2100

ccatccctcg ctccttctcc tacctcatct gggacatcat cgtagcctcc tgcttctact   2160

acgtcgccac cacctacttt cccctcctcc ctcaccctct ctcttacatt gcttggcctc   2220

tctactgggc ctgccaaggc tgcgtcctaa ccggcgtctg ggtcatagcc cacgaatgcg   2280

gccaccacgc tttcagcgac taccagtggc tagacgacac cgtcggtctc atcttccatt   2340

ccttcctcct cgtcccttac ttctcctgga agtacagtca ccgccgtcac cattccaaca   2400

ccggctcg                                                            2408
```

<210> SEQ ID NO 15
<211> LENGTH: 24
<212> TYPE: DNA
<213> ORGANISM: Brassica juncea

<400> SEQUENCE: 15

```
gacttcttgg gagaaggaga aacc                                            24
```

<210> SEQ ID NO 16
<211> LENGTH: 1958
<212> TYPE: DNA
<213> ORGANISM: Brassica juncea

<400> SEQUENCE: 16

```
gaagccaagc acgatcctcc attctcccac ttttagcatt tctttttttt ttttctttct     60

ttccggctac cacttacttg tacttgtaag tcgagtcggt aagaacgttt cctcatatta    120

aactaaagac atcatatatc gtcgccttga tgctaattaa cgtaaccgat gaaaactgta    180

acagaatcca aaccaatctc tctggatatt tggattacca gtgggtcaac caatatttac    240

ttttttttcag aacgaaacac aaaaggaaac ttgataaact ttataaaagt aaacataaat   300

atattcagta ttcactgcct ctttttctgc ttttccgtaa atacataagt gccgtaaata    360

tcagatattt ggaatagaaa agtaataaag gaaaaaaata tgaggagagg aaaaaaagag    420

gggcccagtt gtaaaaaaaa gagagatgtc cactcaatcc tcttctctct cattctttta    480

cccacgggcc gtcaatttaa acggcctagc ttctgcccca tttgcttctg accagaaacc    540

acagagagag agagagtttc attaccaaag agagagagat aggagagaga agatagagag    600

agtctgcgga ggagcttctt cgtagggttc atcgttatta acgttaaatc tctatccccc    660

tacgtcagcc agctcaaggt ccccttcttc ttcttcttct tccatttctt ctcattttac    720

gtttttatc ttcttcaatc ttttgaacct tttctggtct gtggtaatct tattccctct     780

tatcattttg cgcttcaatc gatttcatta tagatctgac aatattgatt gcattcaact    840

atagatctgg tagcgattct ctgtttccat gttaaaatct gttgctgtct tttactattg    900

ttatggttat tgtctatatc gtcgagtata tgaaatgttg cattttcatt ttgttcaaat    960

acgtaagtgt ttgactatct aatttcgatc gttattttta attatatata ttattgatcg   1020

gttggtagag ttgaaaaaaa ttcaccagaa atattatgcg tagcagcctc accgtcctgg   1080

ttataaaatc atcccatctg tttattcaaa agttatatac tactatttgt ttagatctgg   1140

acctgagtat atgtaaagct gtattatctt tgttaaattt gctcctattt gttgaatctt   1200

tggcagattt gaccgattcc tattcgcttc ttggtactgt aattacatag taaatggaaa   1260
```

-continued

```
aattttcatt ggctgcgtgt aaaaaaaaaa aaagaagttc cattgactta tgctagaact   1320

caaactcttg ctcataaacc ttttgtagta caaattaatt gaatatgggg taggtaaact   1380

caggaatctt tcatagattc agatgcaaat agagctgcat gtagaaaata ataggattca   1440

tgacagtaaa aagaagattg gtactatgtt ttgtttgttt ctgtttaaaa gtctatatga   1500

ttgacaataa tatttgttgc tctcaaattc tctctactgt ttcatttagc tttttttttt   1560

ttggccaagt tgatatccaa gaggaatagt gattatggct gctatcttaa aaaaatcgat   1620

atccgcaaga aagagatgtg agctgtagcg tatcaaatct tattcattta ctagtcgtat   1680

tctcaacgct atcgtttatt tctttttctt tcttcggttt gccactaaaa gccgcttccc   1740

tgctctttgt tacacttagt atccattttt gtggtagtcc attttttgaa acgtaacatt   1800

gaatgttttg tctgaaaaaa aaaatttgat ggtttaataa attcttattc tcgcatagac   1860

atttgtcagt taagattaat aagtctttag ctttggacat tgagtttcag ctcctgattg   1920

aagtctttgc ttttgttttt ttttccttgc agaaaaca                           1958
```

<210> SEQ ID NO 17
<211> LENGTH: 1716
<212> TYPE: DNA
<213> ORGANISM: Brassica juncea

<400> SEQUENCE: 17

```
gaagccaagc acgatcctcc attctcaact ttatagcatt tttttctttt ctttccggct     60

accactaact tctacagttc tacttgtgag tcggcaagga cgtttcctca tattaaagta    120

aagacatcaa ataccataat cttaatgcta attaacgtaa cggatgagtt ctataacaca    180

acccaaacta gtctttgtga acattaggat tgggtaaacc aatatttaca ttttaaaaac    240

aaaatacaaa aagaaacgtg ataaacttta taaaagcaat tatatgatca cggcatcttt    300

ttcacttttc cgtaaatata tataagtggt gtaaatatca gatatttgga gtagaaaaaa    360

aaaaaaaaaa aaaagaaata tgaagagagg aaataatgga ggggcccact agtaaaaaag    420

aaagaaaaga gatgtcactc aatcgtctca cacgggcccc cgtcaattta aacggcctgc    480

cttctgccca atcgcatctt accagaacca gagagattca ttaccaaaga gatagagaga    540

gaaagagagg agacagagag agtttgagga ggtgcttctt cgtagggttc atcgttatta    600

acgttaaatc ttcatccccc tacgtcaacc agctcaaggt ccctttcttc ttccatttcc    660

tctcattttt acgttgtttt caatcttggt ctgttctttt cttatcgctt ttctattcta    720

tctatcattt ttgcttttca gtcgatttaa ttctagacct gttaatattt attgcattaa    780

actatagatc tgttcttgat tctctgtttt cttgtgtgaa atcttgatgc tgtctttacc    840

attaatctga ttatattgtc tataccttgg agaatatgaa atgttgcatt ttcatttgtc    900

cgaatacaaa ctgtttgact ttcaatcttt tttaatgatt tattttgatg ggttggtgga    960

gttgaaaaat caccatagca gtctcacgtc ctggtcttag aaatatcctt cctattcaaa   1020

gttatatata tttgtttact tgtcttagat ctggacctga gacatgtaag tacctatttg   1080

ttgaatcttt gggtaaaaaa cttatgtctc tgggtaaaat ttgcttggag atttgaccga   1140

ttcctattgg ctcttgattc tgtaattacg taatacatga aaatgtttc atttggccta    1200

tgctcacttc atgcttataa actttttctt gcaaattaat tggattagat gctccttcat   1260

agattcagat gcaatagatt tgcatgaaga aaataataga attcatgata gtaaaaagat   1320

tgtatttttg tttgtttgtt tatgtttaaa agtctatatg ttgacaatag agttgctatc   1380

aactgtttca tttagtttat gtttttgtca agttgcttat tctaagagac attgtgatta   1440
```

-continued

```
tgacttgtct tctctaacgt agtttagtaa taaaagacga aagaaattga tatccacaag   1500

aaagagatgt aagctgtaac gtatcaaatc tcattaataa ctagtagtat tctcaacgct   1560

atcgtttatt tctttctttg gtttgccact atatgccgct tctctcctct tttgtcccac   1620

gtactatcca tttttttgaa actttaataa cgtaacactg aatattaatt tgttggttta   1680

attaactttg agtttgtttt tggtttatgc agaaac                             1716
```